US008623595B2

(12) United States Patent
Rios

(10) Patent No.: US 8,623,595 B2
(45) Date of Patent: *Jan. 7, 2014

(54) INACTIVATION OF REVERSE TRANSCRIPTASES BY AZIDO-DIARYLPYRIMIDINES

(75) Inventor: Adan Rios, Houston, TX (US)

(73) Assignee: Photoimmune Biotechnology Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/610,260

(22) Filed: Sep. 11, 2012

(65) Prior Publication Data

US 2013/0004534 A1    Jan. 3, 2013

Related U.S. Application Data

(63) Continuation of application No. 12/718,726, filed on Mar. 5, 2010, now Pat. No. 8,367,315.

(51) Int. Cl.
C12Q 1/70    (2006.01)
C12N 5/16    (2006.01)

(52) U.S. Cl.
USPC .............................................. 435/5; 435/339

(58) Field of Classification Search
None
See application file for complete search history.

(56) References Cited

U.S. PATENT DOCUMENTS

| 5,041,078 A | 8/1991 | Matthews et al. ............... 604/4 |
| 5,516,629 A | 5/1996 | Park et al. ......................... 435/2 |
| 5,593,823 A | 1/1997 | Wollowitz et al. ............... 435/2 |
| 5,652,373 A | 7/1997 | Reisner ............................ 800/2 |
| 5,698,767 A | 12/1997 | Wilson et al. .................... 800/2 |
| 5,709,843 A | 1/1998 | Reisner ........................... 424/9.2 |
| 5,849,475 A | 12/1998 | Rovinski et al. .............. 435/69.3 |
| 5,919,458 A | 7/1999 | Aldovini et al. ............. 424/188.1 |
| 6,017,543 A | 1/2000 | Salk et al. ................... 424/208.1 |
| 6,080,408 A | 6/2000 | Rovinski et al. ............. 424/188.1 |
| 6,197,779 B1 | 3/2001 | Andries et al. ................. 514/272 |
| 6,383,806 B1 * | 5/2002 | Rios ........................... 435/339.1 |
| 6,503,753 B1 * | 1/2003 | Rios ............................... 435/339 |
| 6,649,410 B2 * | 11/2003 | Rios ........................... 435/339.1 |
| 6,653,130 B2 * | 11/2003 | Rios ........................... 435/339.1 |
| 7,125,879 B2 | 10/2006 | Guillemont et al. ........... 514/256 |
| 2003/0103940 A1 * | 6/2003 | Slade et al. .................... 424/93.2 |
| 2003/0225114 A1 | 12/2003 | Sommadossi et al. ........ 514/269 |
| 2004/0057930 A1 | 3/2004 | Rios ............................... 435/236 |
| 2008/0039622 A1 | 2/2008 | Singh et al. ................... 544/105 |

FOREIGN PATENT DOCUMENTS

WO    WO 92/11028    7/1992

OTHER PUBLICATIONS

"Aronex HIV inhibitor nears patent issuance," *Reuters NewMedia, Inc.*, Feb. 23, 1996, Abstract
"Aronex reports preliminary clinical results on its HIV integrase inhibitor, zintevir (TM)," *PR Newswire*, Nov. 12, 1996, Abstract. .

Abbas, "Die and let live: eliminating dangerous lymphocytes," *Cell*, 84 (5):655, 1996.
Ada, "An Immunologist's View of HIV Infection," *Textbook of AIDS Medicine*, Chapter 6, pp. 77-87, Brother et al., eds., Williams & Wilkens, Baltimore, MD, 1994.
Ada, "Modern vaccines, the immunological principles of vaccination," *The Lancet*, 335:523-526, 1990.
Albert, et al., "Dendritic cells acquire antigen from apoptotic cells and induce class 1-restricted CTLs," *Nature*, 392:86-89, 1998.
Aldrovandl et al., "The SCID-hu mouse as a model for HIV-1 infection," *Nature*, 363:732-736, 1993.
Amadori et al., "The hu-PBL-SCID mouse in human lymphocyte function and lymphomagenesis studies: achievements and caveats," *Semin Immunol*, 8:249-254, 1996.
Baba et al., "Pathogenicity of live, attenuated hiv after mucosal infection of neonatal macaques," *Science*, 267:1820-1825, 1995.
Bachmann and Zinkernagel, "Neutralizing antiviral b cell responses," *Annu. Rev. Immunol.*, 15:235-270, 1997.
Bader et al., "Oxathiin carboxanilide, a potent inhibitor of human immunodeficiency virus reproduction," *Proc. Natl. Acad. Sci. U.S.A.*, 88 (15):6740-6744, 1991.
Balter, "A cluster of Europe's aids research stars," *Science*, 280:1862, 1998c.
Balter, "Duo brings hope of immune restoration," *Science*, 280:1861, 1998b.
Balter, "Global program struggles to stem the flood of new cases," *Science*, 280:1863-1864, 1998d.
Balter, "HIV incidence: 'more serious than we imagined'," *Science*, 280:1864, 1998e.
Balter, "Modest briton stirs up storm with views on role of CTLs," *Science*, 280:1860-1861, 1998a.
Balter, "T cell production slowed, not exhausted?" *Science*, 283(5400):305-306, 1999.
Baltimore, "Lessons from people with nonprogressive hiv infection," *The New England J. of Medi.*, 332:259-260, 1995.
Balzarini et al., "Identification of novel thiocarboxanilide derivatives that suppress a variety of drug-resistant mutant human immunodeficiency virus type 1 strains at a potency similar to that for wild-type virus," *Antimicrob. Agents Chemother.*, 40 (6):1454-1466, 1996.
Balzarini et al., "Suppression of the breakthrough of human immunodeficiency virus type 1 (HIV-1) in cell culture by thiocarboxanilide derivatives when used individually or in combination with other HIV-1-specific inhibitors (i.e., TSAO derivatives)," *Proc. Natl. Acad. Sci. U.S.A.*, 92 (12):5470-5474, 1995.
Banchereau and Steinman, "Dendritic cells and the control of immunity," *Nature*, 392 (6673):245-252, 1998.
Barnard et al., "The thiocarboxanilide nonnucleoside uc781 is a tight-binding inhibitor of hiv-1 reverse transcriptase," *Biochem.*, 36:7786-7792, 1997.
Barr, "Vaccines for HIV, HIV therapeutic vaccines: the next phase," *GMHC's Treat. Iss.*, vol. 7, No. 5, 1993.
Bender et al., "Inactivated influenza virus, when presented on dendritic cells, elicits human cd8+ cytolytic t cell responses," *J. Exp. Med.*, 12:1663-1671, 1995.
Berger et al., "A new classification of HIV-1," *Nature*,391:340, 1998.
Blauvelt et al., "Productive infection of dendritic cells by HIV-1 and their ability to capture virus are mediated through separate pathways," *J. Clin. Invest.*, 100(8):2043-2053, 1997.

(Continued)

*Primary Examiner* — Craig Ricci
*Assistant Examiner* — Jared D Barsky
(74) *Attorney, Agent, or Firm* — Fulbright & Jaworski LLP

(57) ABSTRACT

Azido-diarylpyrimidine (azido-DAPY) compounds, and compositions containing such compounds, are provided. In addition, methods of using azido-diarylpyrimidines to inactivate reverse transcriptases, prepare inactivated viruses, and treat or prevent viral infections are also provided.

17 Claims, 4 Drawing Sheets

(56) References Cited

OTHER PUBLICATIONS

Boeke, "The unusual phylogenetic distribution of retrotransposons: a hypothesis," *Genome Research*, 1975-1983, 2007.

Bolognesi and Matthews, "Viral envelope fails to deliver?," *Nature*, 391:638-639, 1998.

Bombil et al., "A promising model of primary human immunization inhuman-scid mouse," *Immunobiology*, 195:360-375, 1996 (Abstract).

Borkow et al., "Chemical barriers to human immunodeficiency virus type 1 (hiv-1) infection: retrovirucidal activity of uc781, a thiocarboxanilide nonnucleoside inhibitor of hiv-1 reverse transcriptase," *J. of Virol.*, 71:3023-3030, 1997.

Borkow et al., "Inhibition of the ribonuclease H and DNA polymerase activities of hiv-1 reverse transcriptase by n-(4-tert-butylbenzoyl)-2-hydroxy-1-naphthaldehyde hydrazone," *Biochemistry*, Abstract, 36(11):3179-3185, 1997.

Bryson et al., "Clearance of HIV infection in a perinatally infected infant," *The New Engl. J. of Med.*, 332:833-838, 1995.

Buckheit et al., "Efficacy, Pharmacokinetics, and in Vivo Antiviral Activity of UC781, a Highly Potent, Orally Bioavailable Non-nucleoside Reverse Transcriptase Inhibitor of HIV Type 1," *Aids Res. and Hu. Retro.*, 13:789-796, 1997.

Burr, "Of AIDS and altruism," *U.S. Nws. & W. Rpt.*, pp. 59-61, Apr. 6, 1998.

Burton and Montefiori, "The antibody response in HIV-1 infection," *Aids*, 11:S87-S98, 1997.

Cameron et al., "Dendritic cells and the replication of HIV-1," *J. Leukocyte Biol.*, 59 (2):158-171, 1996.

Cao et al., "Virologic and immunologic characterization of long-term survivors of human immunodeficiency virus type 1 infection," *The New Engl. J. of Med.*, 332:201-216, 1995.

Carlson et al., "Vaccine protection of rhesus macaques against simian immunodeficiency virus infection," *AIDS Res. Hum. Retrovir.*, 6 (11):1239-46, 1990.

Carroll et al., "Inhibition of HIV-1 reverse transcriptase by pyridinone derivatives. Potency, binding characteristics, and effect of template sequence," *J. Biol. Chem.*, 268:276-281, 1993.

Cavert and Haase, "A national tissue bank to track HIV eradication and immune reconstitution," *Science*, 280:1865-1866, 1998.

Cella et al., "Inflammatory stimuli induce accumulation of MHC class II complexes on dendritic cells," *Nature*, 388:782-792, 1997.

Chowdhry, "Photoaffinity labeling of biological systems," *Ann. Rev. Biochem.*, 48:293-325, 1979.

Clerici et al., "HIV-specific t-helper activity in seronegative health care workers exposed to contaminated blood," *JAMA*, 271:42-46, 1994.

Clotet et al., "Long-term survivors of human immunodeficiency virus type I infection," *The New England Journal of Medicine*, 332(24):1646-1647, 1995.

Cohen et al., "Characterization of the binding site for nevirapine (bi-rg-587), a nonnucleoside inhibitor of human immunodeficiency virus type-1 reverse transcriptase," *J. of Biol. Chem.*, 266:14670-14674, 1991.

Collins et al., "HIV-1 Nef protein protects infected primary cells against killing by cytotoxic T lymphocytes," *Nature*, 391:397-402, 1998.

Colonna, "Unmasking the killer's accomplice," *Nature*, 391:642-644, 1998.

Constant and Bottomly, "Induction of TH1 and TH2 $CD4^+$ T cell responses: the alternative approaches," *Annu. Rev. Immunol.*, 15:297-322, 1997.

D'Cruz and Uckun, "Dawn of non-nucleoside inhibitor based anti-HIV microbicides," *Journal of Antimicrobial Chemotherapy*, 57 (3): 411-423, 2006.

Daniel et al., "A role for DNA-PK in retroviral DNA integration," *Science*, 284:644-647, 1999.

Das et al., "Roles of conformational and positional adaptability in structure-based design of TMC125-R165335 (etravirine) and related non-nucleoside reverse transcriptase inhibitors that are highly potent and effective against wild-type and drug-resistant HIV-1 variants," *J. Med. Chem.*, 47 (10):2550-2560, 2004.

DeNoon, "AIDS Therapies: new integrase inhibitor enhances other anti-HIV drugs," *AIDSWEEKLY Plus*, Nov. 23, 1998, Abstract.

Desrosiers et al., "Vaccine protection against simian immunodeficiency virus infection," *Proc. Natl Acad. Sci. USA*, 86 (16):6353-7, 1989.

Doherty and Zinkernagel, "A Biological role for the major histocompatibility antigens," *The Lancet*, 1406-1409, 1975.

Doherty and Zinkernagel, "The Specificity of the Cell Mediated Immune Defense," *The Nobel Assembly at the Karolinska Institute*, Press Release Oct. 7, 1996.

Doolittle, "Immunodeficiency viruses: the simian-human connection," *Nature*, 339 (6223):338, 1989.

Dragic et al., "HIV co-receptors: gateways to the cell," *HIV Advances in Research and Therapy*, 7(3):2-12, 1997.

D'Souza et al., "Neutralization of primary HIV-1 isolates by anti-envelope monoclonal antibodies," *AIDS*, 9:867-874, 1995.

Dutton et al., "T cell memory," *Annu. Rev. Immunol.*, 16:201-223, 1998.

Emerman and Malim, "HIV-1 regulatory/accessory genes: keys to unraveling viral and host cell biology," *Science*, 280:1880-1884, 1998.

Excler and Plotkin, "The prime-boost concept applied to HIV preventive vaccines," *Aids*, 11:S127-S137, 1997.

Ferrari et al., "Clade B-based HIV-1 vaccines elicit cross-clade cytotoxic T lymphocyte reactives in uninfected volunteers," *Proc. Natl. Acad. Sci. USA*, 94: 1396-1401, 1997.

Flavell, "Retroelements, reverse transcriptase and evolution," *Comp. Biochem. Physiol*, 110 (1): 3-15, 1995.

Fletcher et al., "Carboxanilide derivative non-nucleoside inhibitors of HIV-1 reverse transcriptase interact with different mechanistic forms of the enzyme," *Biochemistry* 34(13):4346-4353, Apr. 4, 1995.

Follis et al., "Continued utilization of CCR5 coreceptor by a newly derived T-cell line-adapted isolate of human immunodeficiency virus type 1," *J. Virol.*, 72 (9):7603-7608, 1998.

Frankel and Young, "HIV-1: fifteen proteins and an RNA," *Annu. Rev. Biochem.*, 67:1-25, 1998.

Furman et al., "Phosphorylation of 3'-azido-3'-deoxythymidine and selective interaction of the 5'-triphosphate with human immunodeficiency virus reverse transcriptase," *Proc. Natl. Acad. Sci. U.S.A.*, 83 (21):8333-8337, 1986.

Gallo, "The end or the beginning of the drive to an HIV-preventive vaccine: a view from over 20 years," *The Lancet*, 366: 1854-1898, 2005.

Gibbons et al., "Thy/Liv-SCID-Hu mice implanted with human intestine: an in vivo model for investigation of mucosal transmission of HIV," *AIDS Res Hum Retroviruses*, 13(17):1453-1460, 1997.

Glenn et al., "Skin immunization made possible by cholera toxin," *Nature*, 391:851, 1998.

Goldman et al., "Pyridinone derivatives: specific human immunodeficiency virus type 1 reverse transcriptase inhibitors with antiviral activity," *Proc. Natl. Acad. Sci. U.S.A.*, 88 (15):6863-6867, 1991.

Gotch et al., "New observations on cellular immune responses to HIV and T-cell epitopes," *Aids*, 11:S99-S107, 1997.

Graham and Wright, "Drug therapy, candidate aids vaccines," *Drug Ther.*, 333:1331-1339, 1995.

Grob et al., "Nonnucleoside inhibitors of HIV-1 reverse transcriptase: nevirapine as a prototype drug," *AIDS Res. Hum. Retroviruses*, 8 (2):145-152, 1992.

Guidotti, el al., "Viral clearance without destruction of infected cells during acute HBV infection," *Science*, 284:825-829, 1999.

Hahn, "Viral Genes and Their Products," *Textbook of AIDS Medicine*, Chapter 3, pp. 21-43, Brother et al., eds., Williams & Wilkens, Baltimore, MD, 1994.

Hargrave et al., "Novel non-nucleoside inhibitors of hiv-1 reverse transcriptase, 1. tricyclic pyridobenzo- and dipyridodiazepinones," *J. of Med. Chem.*, 34:2231-2241, 1991.

Harouse, et al., "Distinct pathogenic sequela in rhesus macaques infected with CCR5 or CXCR4 utilizing SHIVs," *Science*, Internet: www.sciencemag.org, 1999.

(56) References Cited

OTHER PUBLICATIONS

Ho et al., "Rapid turnover of plasma virions and CD4 lymphocytes in HIV-1 infection," *Nature*, 373 (6510):123-126, 1995.
Ho, "Toward HIV eradication or remission: the tasks ahead," *Science*, 280:1866-1867, 1998.
Hong et al., "Discovery of HIB-1 integrase inhibitors by pharmacophore searching," *J. Med. Chem.*, 40:930-936, 1997, Abstract.
Huang et al., "Effect of mutations in the nucleocapsid protein (NCP7) upon PR160(GAG-POL) and trna (lys) incorporation into human immunodeficiency virus type 1," *J. of Virology*, 71(6):4378-4384, 1997, Abstract.
Huston, "The biology of the immune system," *JAMA*, 278:1804-1813, 1997.
Hwang et al., "Identification of envelope V3 loop as the major determinant of CD4 neutralization sensitivity of HIV-1," *Science*, 257 (5069):535-537, 1992.
International Preliminary Report on Patentability issued in PCT Application No. PCT/US2011/027164, dated Sep. 12, 2012.
International Search Report issued in PCT/US11/27164, dated Apr. 27, 2011.
Jawetz eds., et al., "Serologic diagnosis & immunologic detection of virus infections," *Lange Medical Book*, 17th ed., Appleton & Lange, Norwalk, CT, pp. 371-380, 1987.
Jing et al., "Potassium-induced loop conformational transition of a potent anti-HIV oligonucleotide," *J. Biomol Struct. Dyn.*, 15:573-583, 1997, Abstract.
Jockusch et al., "Photo-induced inactivation of viruses: adsorption of methylene blue, thionine, and thiopyronine on Qβ bacteriophage," *Proc. Natl. Acad. Sci. USA*, 93:7446-7451, 1996.
Johnson et al., "Inactivated whole-virus vaccine derived from a proviral DNA clone of simian immunodeficiency virus induces high levels of neutralizing antibodies and confers protection against heterologous challenge," *Proc. Natl Acad. Sci. USA*, 89 (6):2175-9, 1992.
Kim et al., "Limitation of Hu-PBL-scid mouse model in direct application to immunotoxicity assessment," *J. Pharmacol Toxicol Methods*, 37:83-89, 1997 (Abstract).
Knight and Patterson, "Bone marrow-derived dendritic cells, infection with human immunodeficiency virus, and immunopathology," *Annu. Rev. Immunol.*, 15:593-615, 1997.
Kollmann et al., "Disseminated human immunodeficiency virus 1 (hiv-1 ) infection in scid-hu mice after peripheral inoculation with hiv-1," *J. Exp. Med.*, 179:513-522, 1994.
Korber, et al., "Limitations of a molecular clock applied to considerations of the origin of HIV-1," *Science*, 280:1868-1871, 1998.
LaCasse et al., "Coreceptor utilization by human immunodeficiency virus type 1 is not a primary determinant of neutralization sensitivity," *J. Virol.* 72 (3):2491-2495, 1998.
LaCasse et al., "Fusion-competent vaccines: broad neutralization of primary isolates of HIV," *Science*, 283:357-362, 1999.
Lamb-Wharton et al., "Primate models of AIDS vaccine development," *Aids*, 11(suppl A):S121-S126, 1997.
Lanzavecchia, "Licence to kill," *Nature*, 393:413-414, 1998.
Le Grand et al., "AIDS vaccine developments," *Nature*, 355 (6362) 684, 1992 (abstract).
Le Grand et al., "Specific and non-specific immunity and protection of macaques against SIV infection," *Vaccine*, 10 (12): 873-879, 1992.
Letvin, "Progress in the development of an HIV-1 vaccine," *Science*, 280:1875-1880, 1998.
Letvin, "Vaccines against human immunodeficiency virus—progress and prospects," *N.E. J. of Med.*, 329:1400-1405, 1993.
Lin et al., "Photoaffinity labeling by 4-thiodideoxyuridine triphosphate of the HIV-1 reverse transcriptase active site during synthesis," *J. Bio. Chem.*, 273:997-1002, 1998.
Lingner et al., "Reverse transcriptase motifs in the ctalytic subunit of telomerase," *Science*, 276: 561-567, 1997.
Loetscher et al., "CCR5 is characteristic of Th1 lymphocytes," *Nature*, 391:344-345, 1998.

Long, "Signal sequences stop killer cells," *Nature*, 391:740-741, 1998.
Ludovici et al., "Evolution of anti-HIV drugs candidates: Part 3: diarylpyrimidine (DAPY) analogues," *Bioorganic and Medicinal Chemistry Letters*, 11 (17): 2235-2239, 2001.
Lundblad, "Telomerase catalysis: a phylogenetically conserved reverse transcriptase," *Proc. Natl. Acad. Sci. USA*, 95: 8415-8416, 1998.
Luster, "Chemokines—chemotactic cytokines that mediate inflammation," *New Engl. J. of Med.*, 338:436-445, 1998.
Martinez, "Positive + Positive: Sex and the risk of reinfection," *Center for AIDS Hope & Remembrance*, 3(6):3-5, 1997.
Matthews et al., "Preliminary studies of photoinactivation of human immunodeficiency virus in blood," *Transfusion*, 31:636-641, 1991.
Mazumder et al., "Curcumin analogs with altered potencies against HIV-1 integrase as probes for biochemical mechanisms of drug action," *J. Med. Chem.*, 40:3057-3063, 1997, Abstract.
McCune et al., "The SCID-hu mouse: murine model for the analysis of human hematolymphoid differentiation and function," *Science*, 241 (4873):1632-1639, 1988.
McIntosh and Burchett, "Clearance of HIV-lessons from newborns," *The New Engl. J. of Med.*, 332:883-884, 1995.
McMichael and Phillips, "Escape of human immunodeficiency virus from immune control," *Annu. Rev. Immunol.*, 15:271-296, 1997.
Meldorf and Corey, "HIV vaccines: combination and prime-boost strategies", HIV: Advances in Research and Therapy, 7(1):25-28, 1997.
Merluzzi et al., "Inhibition of HIV-1 replication by a nonnucleoside reverse transcriptase inhibitor," *Science*, 20 (4986):1411-1413, 1990.
Montefiori and Moore, "Magic of the occult?" *Science*, 283:336-337, 1999.
Mosier et al., "Transfer of a functional human immune system to mice with severe combined immunodeficiency," *Nature*, 335 (6187):256-259, 1988.
Murphey-Corb et al., "A formalin-inactivated whole SIV vaccine confers protection in macaques," *Science*, 246 (4935):1293-7, 1989.
Murphy et al., "The huPBL-SCID mouse as a means to examine human immune function in vivo," *Semin Immunol*, 8:233-241, 1996 (Abstract).
Musey et al., "Cytotoxic-T-cell responses, viral load, and disease progression in early human immunodeficiency virus type 1 infection," *The New England J. of Med.*, 337:1267-1274; 1305-1308, 1997.
Musey et al., "Cytotoxic-T-cell responses, viral load, and disease progression in early human immunodeficiency virus type 1 infection," *N. Eng. J. Med.*, 337(18):1267-1274, 1997.
Nakamura et al., "Telomerase catalytic subunit homologs from fission yeast and human," *Science*, 277: 955-959, 1997.
Namikawa et al., "Infection of the SCID-hu mouse by HIV-1," *Science*, 242-1684-1686, 1988.
NIMH Trial Group, "The NIMH multisite HIV prevention trial: reducing HIV sexual risk behavior," *Science*, 280:1889-1894, 1998.
Office Action, in U.S. Appl. No. 09/249,391, mailed Dec. 19, 2001.
Office Action, in U.S. Appl. No. 09/249,391, mailed Jun. 19, 2001.
Office Action, in U.S. Appl. No. 09/249,391, mailed Jun. 21, 2000.
Office Action, in U.S. Appl. No. 09/638,833, mailed Oct. 2, 2001.
Office Action, in U.S. Appl. No. 10/667,534, mailed Dec. 18, 2009.
Office Action, in U.S. Appl. No. 10/667,534, mailed Jul. 10, 2009.
Office Action, in U.S. Appl. No. 10/667,534, mailed Jun. 26, 2006.
Office Action, in U.S. Appl. No. 10/667,534, mailed May 16, 2007.
Office Action, in U.S. Appl. No. 10/667,534, mailed Oct. 5, 2006.
Oldstone, "HIV versus cytotoxic T lymphocytes—the war being lost," *N. Eng. J. Med.*, 337:1306-1308, 1997.
Osterhaus et al., "Comparison of protection afforded by whole virus ISCOM versus MDP adjuvanted formalin-inactivated SIV vaccines from IV cell-free or cell-associated homologous challenge," *AIDS Res. Hum. Retrovir.*, 8 (8):1507-10, 1992.
Pamer and Cresswell, "Mechanisms of MHC class I-restricted antigen processing," *Annu. Rev. Immunol.*, 16:323-358, 1998.
Pantaleo at al., "Studies in subjects with long-term nonprogressive human immunodeficiency virus infection," *N. Engl. J. Med.*, 332(4):209-216, 1995.

(56) References Cited

OTHER PUBLICATIONS

Pauwels et al., "Potent and selective inhibition of HIV-1 replication in vitro by a novel series of TIBO derivatives," Letters to Nature, 343:470-474, 1990.
Peeters et al., "Virological and polymerase chain reaction studies of HIV-1/HIV-2 dual infection in Côte d'Ivoire," Lancet, 340:339-340, 1992.
Perrin and Telenti, "HIV treatment failure: testing for HIV resistance in clinical practice," Science, 280:1871-1873, 1998.
Phoolcharoen, "HIV/aids prevention in Thailand: success and challenges," Science, 280:1873-1874, 1998.
Piatek et al., "High levels of HIV-1 in plasma during all stages of infection determined by competitive PCR," Science, 259:1749-1754, 1993.
Quinn, "Acute primary HIV infection," JAMA, 278:58-62, 1997.
Ren et al., "Crystal structures of HIV-1 reverse transcriptase in complex with carboxanilide derivatives," Biochem., 37:14394-14403, 1998.
Ridge et al., "A conditioned dendritic cell can be a temporal bridge between a CD4+ T-helper and a T-killer cell," Nature, 393:473-483, 1998.
Robinson, "L-chicoric acid, an inhibitor of human immunodeficiency virus type 1 (HIV-1) integrase, improves on the in vitro anti-HIV-1 effect of zidovudine plus a protease inhibitor (AG1350)," Antiviral Res., 39:101-111, 1998, Abstract.
Robinson, "DNA vaccines for immunodeficiency viruses," Aids, 11:S109-S119, 1997.
Rosenberg et al., "Vigorous HIV-1-specific CD4+ T cell responses associated with control of viremia," Science 278 (5342):1447-1450, 1997.
Rossio et al., "Inactivation of Human Immunodeficiency Virus Type 1 Infectivity with Preservation of Conformational and Functional Integrity of Virion Surface Patterns," J. Virology, 72(10):7992-8001, 1998.
Roth et al., "Synthesis and biological activity of novel nonnucleoside inhibitors of hiv-1 reverse transcriptase. 2-aryl-substituted benzimidazoles," J. of Med. Chem., 40:4199-4205, 1997.
Sabin, "Improbability of effective vaccination against human immunodeficiency virus because of its intracellular transmission and rectal portal of entry," Proc. Natl. Acad. Sci. USA, 89 (18):8852-5, 1992.
Schacker et al., "Annals of internal medicine, biological and virologic characteristics of primary HIV infection," Ann. Intern. Med., 128:613-620, 1998.
Schmitz et al., "Control of viremia in simian immunodeficiency virus infection by cd8' lymphocytes," Science, 283:857-860, 1999.
Schultz, "Changing paradigms for an HIV vaccine," Advances Experi. Med. Biology, 397:79-90, 1996.
Schumacher, "Immunology: accessory to murder," Nature, 398:26-27, 1999.
Seifarth et al., "Rapid identification of all known retroviral reverse transcriptase sequences with a novel versatile detection assay," Aids Research and Human Retroviruses, 16 (8): 721-729, 2000.
Sigal et al., "Cytotoxic T-cell immunity to virus-infected non-haematopoietic cells requires presentation of exogenous antigen," Nature, 398:77-80, 1999.
Smart, "The first integrase inhibitor," GMHC Treat Issues, 10:8-9, 1996, Abstract.
Smerdon et al., "Structure of the binding site for nonnucleoside inhibitors of the reverse transcriptase of human immunodeficiency virus type 1," Proc. Natl. Acad. Sci., USA, 91:3911-3915, 1994.
Springer and Britten, "Phylogenetic relationships of reverse transcriptase and RNase H sequences and aspects of genome structure in the gypsy group of retrotransposons," Phylogeny and Genome Structure of Gypsy Retrotransposons, 1370-1379, 1993.
Stanley et al., "Effect of immunization with a common recall antigen on viral expression in patients infected with human immunodeficiency virus type 1," N. Engl. J. Med., 334 (19):1222, 1996.

Stott and Schild, "Strategies for AIDS vaccines," J. Antimicrobial Chemo., 37(B):185-198, 1996.
Stott et al., "Anti-cell antibody in macaques," Nature, 353 (6343):393, 1991. (abstract).
Sutjipto et al., "Inactivated simian immunodeficiency virus vaccine failed to protect rhesus macaques from intravenous or genital mucosal infection but delayed disease in intravenously exposed animals," J. Virol., 64 (5):2290-7, 1990.
Sylwester et al., "CD4+ T-Lymphocyte Depletion in Human Lymphoid Tissue Ex Vivo Is Not Induced by Noninfectious Human Immunodeficiency Virus Type 1 Virions," J. Virology, 72(11):9345-9347, 1998.
Tang and Cyster, "Chemokine up-regulation and activated T cell attraction by maturing dendritic cells," Science, 284:819-822, 1999.
Tarasiev et al., "Photochemoinactivation: a way to AIDS vaccine?," America Online: ARIOS927, vol. 9 Issue/Part/Supplement 1, 1993 (Abstract).
Valverde-Garduno et al., "Functional analysis of HIV-1 reverse transcriptase motif C: site-directed mutagenesis and metal cation interaction," J. Mol. Evol., 47 (1): 73-80, 1998.
Walker and Burton, "Toward an AIDS vaccine," Science, 320: 760-764, 2008.
Walker, "Immunopathogenesis and immune reconstitution in HIV disease," Intl. Aids Soc.-USA, 6:4-7, 1999.
Wallace et al.,"Preclinical pharmacology of an anti-HIV oligonucleotide," Int. Conf. AIDS, 11:314, 1996, Abstract.
Wang, "Bioorganic approaches towards HIV vaccine design," Current Pharmaceutical Design, 9: 1771-1787, 2003.
Watts, "Capture and processing of exogenous antigens for presentation on MHC molecules," Annu. Rev. Immunol., 15:821-850, 1997.
Weissman et al., "The efficiency of acute infection of CD4+ T cells is markedly enhanced in the setting of antigen-specific immune activation," J. Exp. Med., 183 (2):687, 1996.
Wu et al., "A novel dipyridodiazepinone inhibitor of HIV-1 reverse transcriptase acts through a nonsubstrate binding site," Biochem., 30:2022-2026, 1991.
Wyatt and Sodroski, "The HIV-1 envelope glycoproteins: fusogens, antigens, and immunogens," Science, 280:1884-1888, 1998.
Xu et al., "Human immunodeficiency virus type 1 recombinant reverse transcriptase enzymes containing the G190A and Y181C resistance mutations remain sensitive to etravirine," Antimicrob. Agents Chemother., 53(11):4667-72, 2009.
Yang et al., "Neutralizing antibodies against HIV determined by amplification of viral long terminal repeat sequences from cells infected in vitro by nonneutralized virions," J. AIDS and Human Retrovirology, 17:27-34, 1998.
Zhang et al, "Nascent Human Immunodeficiency Virus Type 1 Reverse Transcription Occurs within an Enveloped Particle," J. Virology, 69(6):3675-3682, 1995.
Zhang et al., "Endogenous reverse transcription of human immunodeficiency virus type 1 in physiological microenviroments: an important stage for viral infection of nondividing cells," J. Virol., 70 (5):2809-2824, 1996.
Zhang et al., "Reverse transcription takes place within extracellular HIV-1 virions: potential biological significance," AIDS Res. Hum. Retroviruses 9 (12):1287-1296, 1993.
Zhao, et al., "Hydrazide-containing inhibitors of HIV-1 integrase," J. Med. Chem., 40:937-941, 1997, Abstract.
Zinkernagel and Doherty, "Immunological surveillance against altered self components by sensitized T lymphocytes in lymphocytic choriomeningitis," Nature, 251:547-548, 1974.
Zinkernagel and Doherty, "MHC-restricted cytotoxic t cells: studies on the biological role of polymorphic major transplantation antigens determining t-cell restriction-specificity, function, and responsiveness," Advan. In Immunol., New York, Academic Press, 27:51-177, 1979.
Zinkernagel and Doherty, "Restriction of in vitro T cell-mediated cytotoxicity in lymphocytic choriomeningitis within a syngeneic or semiallogeneic system," Nature, 248:701-702, 1974.

* cited by examiner

DAPY (TMC120-R147681)

DAPY (TMC125-R165335)

DAPY (R185545)

|  | Concentration | Reverse Transcriptase activity - CPM | | | |
|---|---|---|---|---|---|
|  | nM | Day 5 | Day 10 | Day 16 | Day 30 |
| DAPY | 50 | 475 | 622 | 758 | 310 |
|  | 20 | 6107 | 97742 | 83,106 | 72,512 |
|  | 10 | 5564 | 63659 | 92,443 | 80,920 |
|  | 2 | 14563 | 153,217 | 86,175 | 78,634 |
|  | 0 | 26,512 | 126,531 | 99,412 | 87,318 |
|  | nM | Day 5 | Day 10 | Day 16 | Day 30 |
| DAPY + UV | 50 | 561 | 614 | 308 | 493 |
|  | 20 | 416 | 573 | 842 | 540 |
|  | 10 | 652 | 557 | 42,634 | 97,658 |
|  | 2 | 7531 | 76,004 | 70,316 | 65,218 |
|  | 0 | 42,316 | 89,426 | 67,593 | 80,902 |
|  | nM | Day 5 | Day 10 | Day 16 | Day 30 |
| azido-DAPY + UV | 50 | 642 | 421 | 518 | 470 |
|  | 20 | 308 | 572 | 264 | 382 |
|  | 10 | 416 | 520 | 631 | 865 |
|  | 2 | 294 | 463 | 12,750 | 86,595 |
|  | 0 | 51,352 | 66,807 | 63,771 | 95,738 |
| UV alone | 0 | 26,512 | 126,531 | 99,412 | 87,318 |

FIG. 3

INACTIVATION OF REVERSE TRANSCRIPTASES BY AZIDO-DIARYLPYRIMIDINES

CROSS-REFERENCE TO RELATED APPLICATIONS

This application is a continuation of U.S. application Ser. No. 12/718,726, filed Mar. 5, 2010. The entire contents of the above-referenced disclosure is specifically incorporated herein by reference without disclaimer.

BACKGROUND

1. Field of the Invention

The present invention relates generally to the fields of virology, immunology, disease treatment and prevention. More particularly, it concerns azido-diarylpyrimidines and their use in inactivating reverse transcriptase. Methods of inactivation of viruses and microbes are useful for preventing disease through decreasing the risk of infection associated with exposure to viruses and microbes such as it is the case with the family of retroviruses of which HIV is a member.

2. Description of Related Art

The HIV viruses are members of the Retroviridae family and, more particularly, are classified within the Lentivirinae subfamily. Like nearly all other viruses, the replication cycles of members of the Retroviridae family, commonly known as the retroviruses, include attachment to specific cell receptors, entry into cells, synthesis of proteins and nucleic acids, assembly of progeny virus particles (virions), and release of progeny viruses from the cells. A unique aspect of retrovirus replication is the conversion of the single-stranded RNA genome into a double-stranded DNA molecule that must integrate into the genome of the host cell prior to the synthesis of viral proteins and nucleic acids.

Retrovirus virions are enveloped and contain two copies of the genome. The conversion of the genomic RNA into DNA is provided by the viral protein reverse transcriptase (RT). This protein is bound to the RNA genome within the virion, and its enzymatic conversion of the genome to DNA in many instances start prior to viral entry into the host cell and is completed after viral entry. The initiation of the conversion process may initiate in the virion particles themselves, is known as endogenous reverse transcription (ERT). ERT may be important in increasing the infectivity of HIV in sexual transmission (Zhang et al., 1993, 1996).

Because of the requirement for reverse transcription in the viral replication cycle, compounds that interfere with RT activity have been utilized as anti-HIV therapeutic agents. Many of these compounds, including 3'-azido-2',3'-dideoxythymidine (AZT), are nucleoside analogs that, upon activation by host cell kinases, are competitive inhibitors of reverse transcriptase (Furman et al., 1986). Other anti-RT compounds are nonnucleoside inhibitors (NNI or NNRTI), hydrophobic compounds that do not require cellular modification for antiviral activity. Examples of such compounds include nevirapine (Grob et al., 1992; Merluzzi et al., 1990), the pyridinones (Carroll et al., 1993; Goldman et al., 1991), and the carboxanilides (Bader et al., 1991; Balzarini et al., 1995, 1996). The nevirapine analog 9-azido-5,6-dihydro-11-ethyl-6-methyl-11H-pyrido[2,3-b][1,5]benzodiazepin-5-one (9-AN) and the carboxanilide analog N-[4-chloro-3-(3-methyl-2-butenyloxy)phenyl]-2-methyl-3-furanocarbothiamide (UC781™) have been shown to be potent inhibitors of RT. Compounds, including azido-labeled compounds, for the photoinactivation of reverse transcriptase are disclosed in U.S. Pat. Nos. 6,653,130; 6,649,410; 6,503,753; and 6,383,806, each of which is incorporated herein by reference.

A series of anti-HIV candidate DAPY analogues were published by Ludovici (Ludovici et al., 2001), which is incorporated herein by reference. DAPY compounds, such as dapivirine and etravirine, have shown great potency in inhibiting the activity of HIV reverse transcriptase. While these are capable of binding reverse transcriptase, the binding is reversible. Thus, eventually the reverse transcriptase can escape inactivation by the DAPY compound. Accordingly, there is a need for compounds and methods that can permanently inactivate reverse transcriptase activity.

SUMMARY OF THE INVENTION

In one embodiment, the present invention provides an azido-diarylpyrimidine (azido-DAPY). The DAPY structure of the azido-DAPY may be derived from any DAPY including, but not limited to, dapivirine, etravirine, and R185545. The azido group may be bound to any carbon in the azido-DAPY. The azido-DAPY may have one azido group or multiple azido groups, e.g., 2, 3, 4, 5, or 6 azido groups, or any range derivable therein.

In one embodiment, the present invention provides an azido-diarylpyrimidine compound having the formula of formula (I):

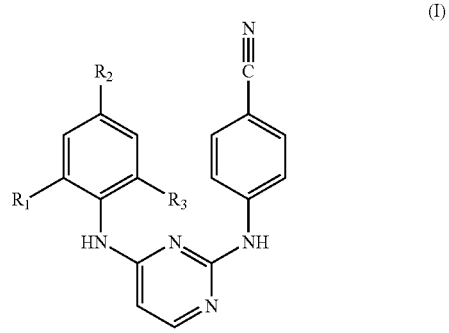

wherein $R_1$, $R_2$, and $R_3$ are independently $N_3$ or lower alkyl, with the proviso that at least one of $R_1$, $R_2$, and $R_3$ is $N_3$.

In certain embodiments, the present invention provides an azido-diarylpyrimidine compound having the formula of formula (II), (III), or (IV):

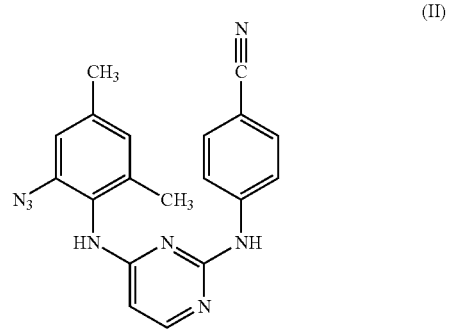

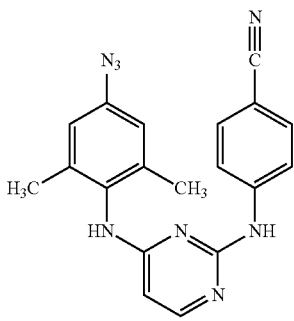

(III)

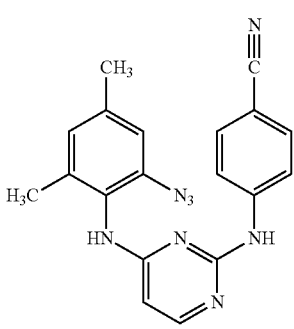

(IV)

It will be understood by those in the art that the azido group may be represented in a chemical structure as $N_3$ or as:

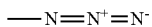

The term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. Unless the number of carbons is otherwise specified, "lower alkyl" as used herein means an alkyl group, as defined above, but having from 1 to 6 carbon atoms in its backbone structure. In particular embodiments, the alkyl group is —$CH_3$.

In other embodiments, the present invention provides a composition comprising an azido-diarylpyrimidine (azido-DAPY) and a pharmaceutically acceptable carrier. In certain aspects of the invention, the composition comprises a compound having the formula of formula (I) and a pharmaceutically acceptable carrier. In some embodiments, the composition comprises a compound having the formula of formula (II), (III), or (IV), and a pharmaceutically acceptable carrier. The composition may comprise a combination of two or more different azido-diarylpyrimidine, such as, for example, a combination of compounds having the formulas of formulas (II), (III), and (IV).

In certain embodiments, the composition comprising the azido-diarylpyrimidine and the pharmaceutically acceptable carrier may further comprise a contraceptive. In some embodiments the composition comprising the azido-diarylpyrimidine and the pharmaceutically acceptable carrier may further comprise at least a second anti-viral agent. Non-limiting examples of such anti-viral agents include 3"-azido-2",3"-dideoxythymidine (AZT), nevirapine, pyridinones, carboxanilides, 9-azido-5,6-dihydro-11-ethyl-6-methyl-11H-pyrido[2,3-b][1,5]benzodiazepin-5-one (9-AN), and N-[4-chloro-3-(3-methyl-2-butenyloxy)phenyl]-2-methyl-3-furanocarbothiamide (UC781™). The composition may be formulated for a variety of routes of administration including, but not limited to, topical formulations, vaginal formulations, rectal formulations, oral formulations, or injectible formulations. In some embodiments, the composition is formulated for delivery to the mucosa. The composition may be formulated as, for example, a suppository, pessary, cream, film, foam, gel, paste, mouthwash, eye drop, liquid, aerosol, or spray. In some embodiments the composition further comprises a bioadhesive. In other embodiments, the composition is formulated as a pill, tablet, capsule, or an injectible solution. In certain aspects of the invention, the composition is formulated or impregnated in, for example, a ring, sponge, tampon, bandage, or swab.

In some embodiments, the composition comprises up to about 50%, 40%, 30%, 25%, 20%, 15%, 10%, 9%, 8%, 7%, 6%, 5%, 4%, 3%, 2%, 1%, or 0.5% by volume of the azido-diarylpyrimidine. In other embodiments, the composition comprises at least 50%, 40%, 30%, 25%, 20%, 15%, 10%, 9%, 8%, 7%, 6%, 5%, 4%, 3%, 2%, 1%, or 0.5% by volume of the azido-diarylpyrimidine. In certain embodiments, the composition comprises between about 0.1 to 50%, 1 to 50%, 0.5 to 20%, 1 to 20%, 0.1 to 10%, 1 to 10%, 1 to 5%, or 1 to 2% by volume of the azido-diarylpyrimidine.

In one embodiment, the present invention provides a method of inactivating a reverse transcriptase comprising contacting a reverse transcriptase with an azido-diarylpyrimidine; and irradiating the reverse transcriptase and the azido-diarylpyrimidine with ultraviolet light to inactivate the reverse transcriptase. In certain embodiments, the azido-diarylpyrimidine has the formula of formula (I). In particular embodiments, the azido-diarylpyrimidine has the formula of formula (II), (III), or (IV).

It is contemplated that any light that causes the reaction of the azido compound with RT may be used. In one embodiment, the light is a UV light. In certain embodiments, the UV light has a wavelength of between about 10 to 400 nm, 200 to 400 nm, or 300 to 400 nm. In certain aspects, the UV light has a wavelength of at least 254 nm or a wavelength of at least 300 nm. In one embodiment the UV light is that emitted by a GE 275 W sun lamp.

In another embodiment, the present invention provides a composition comprising a retrovirus particle and an azido-diarylpyrimidine. In certain embodiments, the azido-diarylpyrimidine has the formula of formula (I). In particular embodiments, the azido-diarylpyrimidine has the formula of formula (II), (III), or (IV). The retrovirus particle may be, for example, a lentivirus particle, alpharetrovirus particle, betaretrovirus particle, gammaretrovirus particle, deltaretrovirus particle, epsilonretrovirus particle, or spumavirus particle. In certain embodiments, the lentivirus particle is a human immunodeficiency virus (HIV) particle.

In yet another embodiment, the present invention provides a composition comprising a Hepatitis-C particle and an azido-diarylpyrimidine. In certain embodiments, the azido-diarylpyrimidine has the formula of formula (I). In particular embodiments, the azido-diarylpyrimidine has the formula of formula (II), (III), or (IV).

In a further embodiment, the present invention provides a composition comprising a hepadnovirus particle and an azido-diarylpyrimidine. In certain embodiments, the azido-diarylpyrimidine has the formula of formula (I). In particular embodiments, the azido-diarylpyrimidine has the formula of formula (II), (III), or (IV).

In one embodiment, the present invention provides a method of inactivating a retrovirus, hepatitis-C virus, or hepadnavirus comprising contacting a retrovirus, hepatitis-C virus, or hepadnavirus with an azido-diarylpyrimidine; and irradiating the virus and the azido-diarylpyrimidine with ultraviolet light to inactivate the virus. In certain embodiments, the azido-diarylpyrimidine has the formula of formula (I). In particular embodiments, the azido-diarylpyrimidine has the formula of formula (II), (III), or (IV). The retrovirus particle may be, for example, a lentivirus particle, alpharetrovirus particle, betaretrovirus particle, gammaretrovirus particle, deltaretrovirus particle, epsilonretrovirus particle, or spumavirus particle. In certain embodiments, the lentivirus particle is a human immunodeficiency virus (HIV) particle.

In another embodiment, the present invention provides a method of eliciting an immune response comprising administering a retroviral particle, hepatitis-C particle, or hepadnaviral particle, comprising a reverse transcriptase covalently bound to an azido-diarylpyrimidine to a subject, wherein an immune response is elicited in the subject. In certain aspects of the invention, the azido-diarylpyrimidine was covalently bound to the reverse transcriptase by UV irradiation. The methodology is applicable to any retroviral pathogen. The subject may be any animal including, but not limited to humans, cats, dogs, horses, sheep, cows, goats, mice, rats, rabbits, or birds. The subject may be, for example, mammal, primate, rodent, avian, equine, ovine, bovine, caprine, feline, or canine.

The term "treatment" refers to the administration or application of a remedy or remedies to a patient for a disease or an injury. The treatment need not to effect the cure or prevention of a disease or injury, although a cure or prevention may be achieved in some patients receiving treatment. A treatment may be prophylactic in that it is administered before the patient has the disease (e.g., prior to exposure to the pathogen or after exposure but prior to development of symptoms) or injury that is being treated, or treatment may be therapeutic in that it is administered to a patient who has the disease or injury.

The use of azido-diarylpyrimidines, which have been shown to bind and inactivate reverse transcriptase, permits the generation of non-infectious particles of any virus that requires a reverse transcriptase (RT) in its replication cycle upon exposure of infectious particles to the compound. Irradiation of the azido-diarylpyrimidine and the virus with UV light increases the ability of the compound to inactivate reverse transcriptase. The effective inactivation of RT by the methods described herein allows the production of non-infectious particles of any virus that requires a reverse transcriptase (RT) in its replication cycle including, for example, HIV. These non-infectious particles have the capacity of eliciting an effective cell mediated and antibody mediated immune response that is protective against infection by the virus. The inactivated particles preserve the antigenic composition of infectious wild-type particles and thereby facilitate the dendritic cell-mediated processing and presentation of particle-derived antigens to T cells. The inactivated particles are effective immunogens. The application of this methodology to different strains of HIV allows the production of a polyvalent HIV vaccine. The inactivated HIV particles upon binding to CD4 receptors will expose epitopes that may elicit broad immunogenic responses capable of inhibiting the infectivity of diverse types of HIV from different clades.

The use of azido-diarylpyrimidines as described herein, also permits the prevention or inhibition of infection by any virus that requires a reverse transcriptase (RT) in its replication cycle, because such viruses are inactivated upon exposure to the compound. Irradiation of the azido-diarylpyrimidine and the virus with UV light increases the ability of the compound to inactivate reverse transcriptase and thereby inactivate the virus particle. As used herein, "infection" refers to the invasion of a body or cell by pathogenic microorganisms and their multiplication within the body or cell. Thus, while a retrovirus inactivated as described herein may be able to enter a body or cell, it is not capable of infection because it cannot multiply. The azido-diarylpyrimidines may be used according to the methods described herein as a microbicide to inactivate viral particles containing reverse transcriptase. Such microbicides may be used, for example, to surface that have come into contact with or may come into contact with viral particles containing reverse transcriptase. For example, the microbicide may be in a contraceptive or non-contraceptive formulation applied to the vagina to reduce the risk of transmitting HIV during sexual intercourse. Preferably, such a formulation is applied prior to sexual intercourse, but some benefit may be obtained for the woman if the microbicide is applied promptly after intercourse. As a further example, the microbicide may be applied topically, particularly to wounds or other breaks in the skin to reduce the risk of transmitting HIV via the break in the skin. As noted above, irradiation of the azido-diarylpyrimidine and the virus with UV light increases the ability of the compound to inactivate reverse transcriptase. Accordingly, in certain embodiments, the microbicide is irradiated after it is applied to the treatment site.

The methods described herein may be used to inactivate any virus particle that require a reverse transcriptase for their replication cycle. HIV and Human T-Lymphotropic Virus are examples of human pathogens that falls within the category. Feline leukemia virus, feline immunodeficiency virus, avian leukosis virus, bovine leukemia virus, and rous sarcoma virus, are examples of retroviral pathogens of veterinary significance.

In particular embodiments, the virus particle is an HIV particle. The HIV particle may be any type, subtype or isotype of HIV. In one embodiment, the HIV particle is a wild type HIV particle. In certain embodiments the HIV particle is HIV 1. The HIV 1 particle may be Group M, N, or O. In some embodiments the Group M HIV 1 may be clade A, clade B, clade C, clade D, clade E, clade F, clade G, clade H, or clade I. In one embodiment of the invention, the Group M particle is a clade B particle.

A further aspect of the present invention is a method of determining the presence of retroviral antigens in a sample, comprising immunizing a host with one or more inactivated viral particles as described herein to generate viral-specific antibodies, contacting these antibodies with the sample so that complexes of sample antigens and antibodies are produced, and determining the production, presence, or abundance of these complexes.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, device, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, device, or system that "comprises," "has," "contains," or "includes" one or more recited features possesses those features, but is not limited to possessing only those features; it may possess features that are not recited.

Any embodiment of any of the present methods, devices, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawing forms part of the present specification and is included to further demonstrate certain aspects of the present invention. The invention may be better understood by reference to one or more of these drawings in combination with the detailed description of specific embodiments presented herein.

FIG. 3. A table showing data from a study demonstrating UV inactivation of HIV in MT-2 cells by azido-DAPY. The inactivation of HIV was evaluated by a reverse transcriptase activity assay in which the measurements are provided in counts per minute (cpm).

DESCRIPTION OF ILLUSTRATIVE EMBODIMENTS

Retroviruses and Reverse Transcriptase

The Retroviridae family includes the lentivirus, alpharetrovirus, betaretrovirus, gammaretrovirus, deltaretrovirus, epsilonretrovirus, and spumavirus genera. The Human Immunodeficiency Virus (HIV), which is a lentivirus, is perhaps the best known retroviral pathogen in humans. Retroviruses store their nucleic acid in the form of a +mRNA genome. After a retrovirus enters a host cell, the single-stranded RNA undergoes reverse transcription in the cytosol to form a double-stranded DNA molecule that must then be integrated into the host's genome prior to the synthesis of viral proteins and nucleic acids. Accordingly, all retroviruses possess a reverse transcriptase enzyme, which converts the RNA of their genetic material into DNA. Since retroviruses cannot integrate into the genetic machinery of the host cell without reverse transcription, the inhibition of reverse transcriptase has as a universal consequence on the inability of any retrovirus to integrate within the genetic machinery of a suitable host cell. Thus, regardless of the type of retrovirus, the inactivation of reverse transcriptase as described in the present specification would be understood by a person of ordinary skill in the art to be applicable to any virus that depends on reverse transcription in its replication cycle. Due to the importance of RT to retroviruses, a number of anti-retroviral compounds that interfere with RT activity have been developed (e.g., AZT, nevirapine, pyridinones, carboxanilides).

Azido-Diarylpyrimidines

Figure 1:
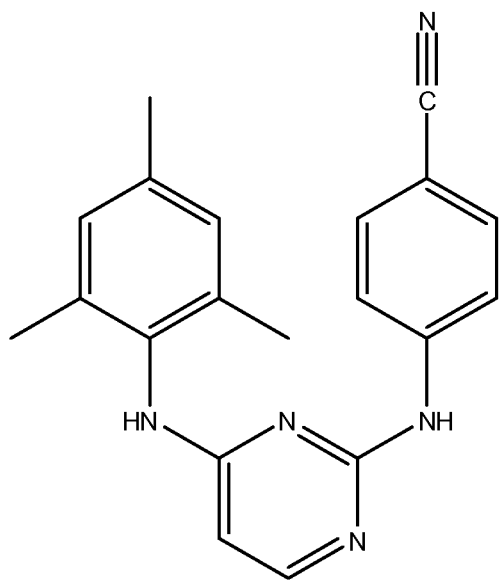
FIG. 1. Chemical structures of three DAPY compounds—TMC120-R147681, TMC125-R165335, and R185545.
Figure 1:
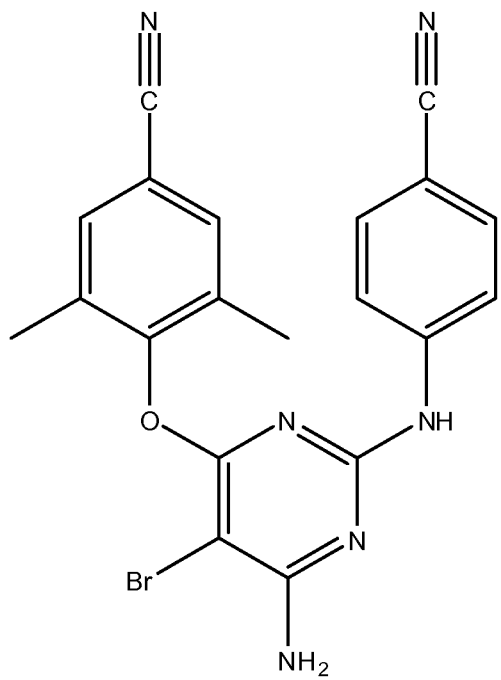
Figure 1:
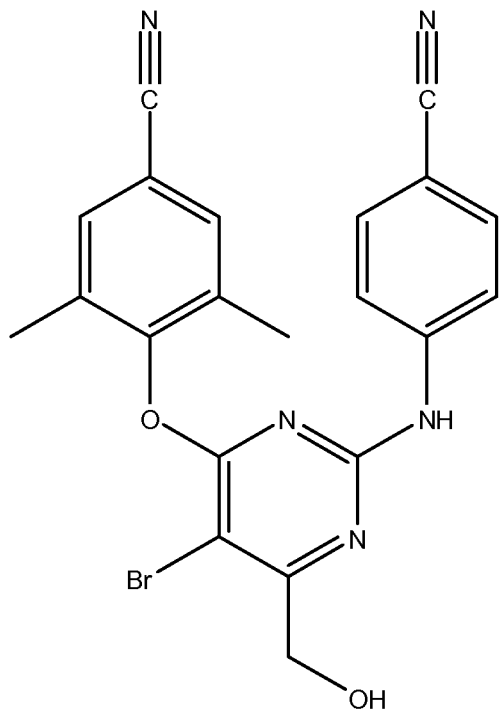

Various embodiments of the present invention provide azido-diarylpyrimidine (azido-DAPY) compounds. As demonstrated herein, azido-DAPY compounds are particularly effective at inactivating reverse transcriptase and consequently inactivating viruses that rely on reverse transcriptase to replicate. The DAPY structure of the azido-DAPY may be derived from any DAPY including, but not limited to dapivirine and etravirine. Diarylpyrimidines (DAPY) are non-nucleoside reverse transcriptase inhibitors (NNRTIs). A series of anti-HIV candidate DAPY analogues were published by Ludovici (Ludovici et al., 2001), which is incorporated herein by reference. DAPY compounds, such as dapivirine and etravirine, have shown great potency in inhibiting the activity of HIV reverse transcriptase. The chemical structures of dapivirine (TMC120-R147681) and etravirine (TMC125-R165335) are provided in FIG. 1.

Diarylpyrimidines can bind RT in multiple conformations and thereby escape the effects of drug-resistance mutations. Structural studies have shown that etravirine (TMC125-R165335) and other DAPY analogues can adapt to changes in the non-nucleoside reverse transcriptase inhibitor (NNRTI) binding pocket in several ways: (1) DAPY analogues can bind in at least two conformationally distinct modes; (2) within a given binding mode, torsional flexibility ("wiggling") of DAPY analogues permits access to numerous conformational variants; and (3) the compact design of the DAPY analogues permits significant repositioning and reorientation (translation and rotation) within the pocket ("jiggling") (Das et al., 2004), incorporated herein by reference). These adaptations provide potency against wild-type and a wide range of drug-resistant mutant HIV-1 RTs.

Hydrophobic DAPYs can readily enter the lipid bilayer of the cell plasma membrane and are sequestered in cellular compartments that enables access to HIV during subsequent virus exposure. Fusion of incoming virus with the drug-treated cell membrane is thought to allow diffusion of the intra-cellular DAPY into the virion, thereby allowing binding to HIV-1 RT within (see Cruz and Uckun, 2006), incorporated herein by reference). Due to their rapid association rate and a very slow dissociation rate, reverse transcription would be inhibited for prolonged periods following fusion and entry, thereby preventing the cell from becoming infected as well as resulting in attenuated infectivity of virions.

The azido-DAPY compounds disclosed herein, comprise an azido group as part of their structure. The azido group may be bound to any carbon in the azido-DAPY. The azido-DAPY may have one azido group or multiple azido groups, e.g., 2, 3, 4, 5, or 6 azido groups, or any range derivable therein. Although conventional diarylpyrimidines are tight binders in the hydrophobic pocket of reverse transcriptases, their binding is reversible. Thus, the RT can eventually separate from the DAPY molecule to regain its functional capacity. The presence of the azido group provides the azido-DAPY compounds with the ability upon irradiation with UV light to photoactivate to form an irreversible covalent bond in the hydrophobic pocket of reverse transcriptases. Accordingly, by using azido-DAPY compounds in conjunction with UV light, reverse transcriptases can be permanently inactivated.

Figure 4:
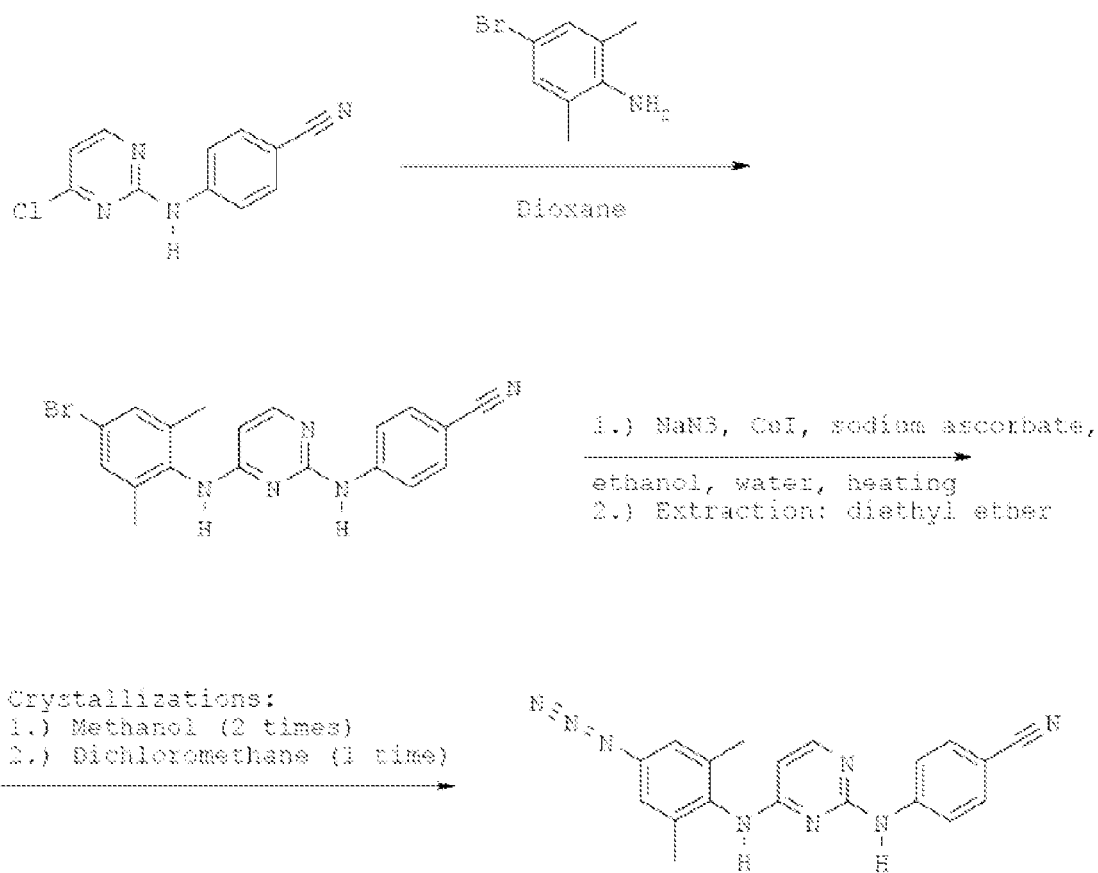
FIG. 4. A chemical synthesis scheme for making an azido-DAPY compound.

The azido-DAPY compounds may be produced from DAPY compounds by diazotization with sodium nitrite followed by a reaction with sodium azide. With this method, the azido group is not directed to a specific location on the DAPY molecule. This, however, is not an issue for inactivating RTs because the photoactivation of the azido group can covalently bind the azido-DAPY to the RT regardless of the position at which the azido group is added through this synthesis. Furthermore, magnetic resonance analysis of the azido-DAPY compounds may be used to determine the location of the azido group, if desired. Methods for the synthesis of DAPY compounds are described in Ludovici (Ludovici et al., 2001). Another method for synthesizing azido-DAPY compounds is shown by the chemical synthesis scheme in FIG. 4. As can be seen in this scheme, the bromine group directs the location of the azido group. Thus, it will be understood by those in the art that a similar scheme could be used to synthesize azido-DAPY compounds with the azido group at different positions by starting with the bromine at the desired position. It will also be understood that one could use different chloropyrimidine groups in this synthesis scheme in order to synthesize different azido-DAPY compounds.

Photoinactivation of Reverse Transcriptase

As mentioned above, azido-DAPY compounds can form an irreversible covalent bond in the hydrophobic pocket of reverse transcriptases when used in conjunction with UV light, thus resulting in the photoinactivation of reverse transcriptase. Any exposure to light that causes the reaction of the azido compound with RT may be used. Although UV light above 254 nm wavelength, such as that emitted by a GE 275 W sun lamp, is preferred. UV light having a wavelength of at least 254 nm or more preferably at least 300 nm are recommended for applications were it is desirable to avoid protein degradation by the UV light.

Several methods of photoinactivation of retroviruses have been reported. U.S. Pat. No. 5,041,078, for example, describes the use of sapphyrins in the photodynamic inactivation of viruses, including HIV. U.S. Pat. Nos. 5,516,629 and 5,593,823 describe the use of psoralens and ultra violet light to inactivate HIV. Methods of photoinactivation retroviruses using azido-labeled compounds are disclosed in U.S. Pat. Nos. 6,653,130; 6,649,410; 6,503,753; and 6,383,806, each of which is incorporated herein by reference. U.S. Pat. Nos. 5,041,078, 5,516,629, and 5,593,823 are incorporated herein by reference. Attempts to inactivate viruses using photosensitizers and light have also been developed using some non-psoralen photosensitizers. The photosensitizers that have been employed are typically dyes. Examples include dihematoporphyrin ether (DHE), Merocyanine 540 (MC540) and methylene blue.

Carlson et al. (1990) has shown that a psoralen-inactivated whole SIV (the Simian counterpart of HIV) vaccine can protect against low challenge doses of SIV and prevent early death in those monkeys that do become infected, suggesting that inactivated HIV may be an effective vaccine in humans. However, because photoinactivation using psoralens is dependent on two rare events, the localization of the psoralen into sites with two thymines (or uracils) present and its sequential absorption of 2 UVA photons, a more efficient method of inactivation is preferable to decrease the likelihood of live virus within a sample. Furthermore, these methods alter the antigenic conformation of HIV affecting the production of an effective immunological response.

Pharmaceutical Compositions

The azido-diarylpyrimidine compounds may be formulated in pharmaceutical compositions (e.g., microbicides) or they may be used to inactivate virus particles that are then formulated in pharmaceutical compositions (e.g., vaccines). The inactivation of the virus by photoinactivation of RT provides noninfectious, immunogenic particles that are essentially identical in conformation and composition as the infectious particles. Therefore, the particles inactivated in this manner are ideal for use as candidate vaccines against retroviral diseases, and in particular HIV diseases including AIDS and AIDS-related conditions. Thus, in certain embodiments the present invention provides an immunogenic composition that may be used as a vaccine against retroviral infection, including HIV infection and its consequences, including AIDS and AIDS-related conditions.

The immunogenic composition may also be used to generate diagnostic antibodies, retrovirus-binding compounds, and diagnostic kits useful in the development of vaccines. The immunogenic compositions elicit an immune response, which produces cellular and humoral immune responses that are antiviral. A vaccinated host can be the source of diagnostic antibodies. If a vaccinated host is challenged by the retrovirus, T cells of the cellular response will eliminate infected cells and antibodies of the humoral response will inactivate the virus by binding to its surface.

Vaccines may be injectable liquid solutions or emulsions. The RT-inactivated virus particles may be mixed with pharmaceutically-acceptable excipients which are compatible with the inactivated virus particles. By compatible it is meant that the pharmaceutically-acceptable excipients will not alter the conformational characteristics of the viral particle. Excipients may include water, saline, dextrose, glycerol, ethanol, or combinations thereof. The vaccine may further contain auxiliary substances, such as wetting or emulsifying agents, buffering agents, or adjuvants to enhance the effectiveness of the vaccines. Adjuvants may be mineral salts (e.g., $AlK(SO_4)_2$, $AlNa(SO_4)_2$, $AlNH_4(SO_4)$, silica, alum, $Al(OH)_3$, $Ca_3(PO_4)_2$, kaolin, or carbon), polynucleotides (e.g., poly IC or poly AU acids), and certain natural substances (e.g., wax D from *Mycobacterium tuberculosis*, substances found in *Corynebacterium parvum*, *Bordetella pertussis*, or members of the genus *Brucella*) (PCT Application No. 91/09603). Aluminum hydroxide or phosphate (alum) are commonly used at 0.05 to 0.1 percent solution in phosphate buffered saline. Other adjuvant compounds include QS21 or incomplete Freunds adjuvant.

Vaccines may be administered parenterally, by injection subcutaneously or intramuscularly, or the vaccines may be formulated and delivered to evoke an immune response at the mucosal surfaces. The immunogenic composition may be administered to a mucosal surface by the nasal, oral, aerosolized nebulations, vaginal, or anal routes. In certain embodiments, the immunogenic composition is administered to a mucosal surface that is likely to be challenged by HIV, such as the anal, vaginal, and/or oral mucosa. For vaginal or anal delivery, suppositories may be used. Suppositories may comprise binders and carriers such as polyalkalene glycols or triglycerides. Oral formulations may be in the form of pills, capsules, suspensions, tablets, or powders and include pharmaceutical grades of saccharine, cellulose or magnesium carbonate. These compositions may contain 1% to 95% of the RT-inactivated viral particles.

The vaccine should be administered in such a way as to elicit an immune response to the RT-inactivated viral particles. Suitable doses required to be administered are readily discernible by those of skill in the art. Suitable methodologies for the initial administration and booster doses, if necessary, maybe variable also. The dosage of the vaccine may depend on the route of administration and may vary according to the size of the host. One of skill in the art may obtain details regarding the practice and use of HIV vaccines in the American Foundation for AIDS Research's HIV Experimental Vaccine Directory (1998), which is hereby incorporated by reference in its entirety.

Although the immunogenic compositions of the present invention may be administered to individuals that are not infected with the retrovirus, retrovirus-negative, they also may be administered to individuals who are infected with the virus in an effort to alter the immune response to the virus. The alteration may be a stimulation of anti-retrovirus CD4+ or CD8+ T cells, an increase in antibody production, or in respect to the type of response to the virus (i.e., TH1 vs. TH2). Nonetheless, this alteration if effective will decrease the mortality and morbidity associated with the infection. In other words, the immunogenic compound may decrease the severity of the disease and increase the life of the patient.

Where clinical application of an immunogen according to the present invention is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

In other embodiments, the azido-diarylpyrimidine compounds may be formulated in pharmaceutical compositions. Such compositions may be used to inactivate retrovirus. For example, a pharmaceutical composition comprising an azido-diarylpyrimidine may be administered orally to treat a retrovirus infection in a subject. As another example, a pharmaceutical composition comprising an azido-diarylpyrimidine may be administered topically, particularly to areas believed to be at risk for the transmission of the virus. With HIV, for example, topical application of a pharmaceutical composition comprising an azido-diarylpyrimidine to mucus membranes in the vagina, rectum, and/or oral cavity may be used to inactivate HIV that may be transmitted during sexual activity. These anti-viral topical formulations may also be referred to as "microbicides." In certain embodiments, the microbicide is irradiated after it is applied to the treatment site. In some embodiments, the treated site is irradiated for between about 5 to 10 or 5 to 20 minutes.

Several NNRTIs are currently under development as candidate microbicides to inhibit cell-free as well as cell-associated HIV-1 replication in genital tract secretions. A review of anti-HIV microbicides is provided in Cruz and Uckun (2006), which is incorporated herein by reference. NNRTIs, such as DAPY compounds, have an advantage over nucleoside analogue RT inhibitors as microbicides because NNRTIs do not require metabolic activation to achieve anti-viral activity. Vaginal or rectal formulations can be administered as a suppository or pessary. Other vaginal or rectal preparations may include creams, films, foams, gels, pastes, rings, sponges, sprays, or tampons containing the azido-diarylpyrimidine and acceptable carriers. In certain embodiments, the composition may include a spermacide. These microbicidal compositions may comprise between about 0.1 to 50% by volume of the azido-diarylpyrimidine. In some embodiments, the composition may contain one or more additional anti-viral agents. In one aspect of the invention, the azido-diarylpyrimidine is formulated in a microemulsion (e.g., GM-144) or self-emulsifying gel (e.g., Conceival).

The carrier in a microbicide formulation may comprise a mucoadhesive. Mucoadhesives aid in retaining the antigen at or near the mucosa for a sufficient period of time to ensure adequate bioavailability of the azido-diarylpyrimidine. The mucoadhesive may be a polymer, such as a polyethylene oxide homopolymer, poly vinyl pyrrolidone (PVP), methyl cellulose (MC), sodium carboxy methylcellulose (SCMC), hydroxy propyl cellulose (HPC), Carbopol, polyacrylate, chitosan, or polysaccharide. In one embodiment, the mucoadhesive is derived from Aloe vera polyshaccharides. The mucoadhesive polymer may be hydrophilic or a hydrogel.

Aqueous compositions of the present invention comprise an effective amount of the azido-diarylpyrimidine or inactivated virus, dissolved or dispersed in a pharmaceutically acceptable carrier or aqueous medium. The phrases "pharmaceutically acceptable" or "pharmacologically acceptable" refer to molecular entities and compositions that do not produce an adverse, allergic or other untoward reaction when administered to a subject, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the pharmaceutical compositions is contemplated. Supplementary active ingredients also can be incorporated into the compositions.

Administration of pharmaceutical compositions according to the present invention will be via any common route so long as the target tissue is available via that route. This includes oral, nasal, aerosol, buccal, ocular, rectal, vaginal or dermal. Alternatively, administration will be by orthotopic, intradermal, intraocular, subcutaneous, intramuscular, intraperitoneal or intravenous injection. Such compositions would normally be administered as pharmaceutically acceptable compositions that include physiologically acceptable carriers, buffers or other excipients.

In certain embodiments, the pharmaceutical compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components of the pharmaceutical composition are adjusted according to well known parameters.

The compositions of the present invention may comprise a supplement of one or more compounds capable of preventing or inhibiting the replication of a retrovirus, including the compound utilized to inactivate the virus. These compounds may include, but are not limited to, nucleoside analog inhibitors of HIV RT (e.g., AZT), non-nucleoside inhibitors of HIV-RT (e.g., UC781™), or HIV protease inhibitors.

Safety of the Immunogens

The safety of immunogens may be demonstrated by their inability to produce infection in susceptible cells regardless of the amount of particles used as inoculum. Controlled studies may be conducted by exposing susceptible cells to increased concentrations of these particles. Particles that have their RT inactivated will fail to infect susceptible cells, while the control studies will maintain the capacity to produce infection in the susceptible cells. The same methodology that was used to generate the viral particles may be used to test the inactivation of the virus particles. One approach to monitor infectivity in both the non-infectious particles and the controls is to monitor the production of RT and p24 antigen in the culture supernatants. In one embodiment, supernatants are tested for the presence of virus particles by the sensitive method of heminested polymerase chain reaction (HNPCR) amplification of the 5' LTR sequences (LTR-HNPCR). This test will confirm the absence of infectivity of the particles since there is an excellent correlation between a negative infectivity test and a negative LTR-HNPCR (Yang et al., 1998).

The safety of the particles can also be evaluated in vivo by inoculation of the animal models discussed below. The lack of infectivity of the inactivated particles can be determined by repeated high dose inoculation of animals such as PBL-SCID mice, SCID-hu mice, or non-human primates.

As a way of creating an additional safety mechanism for the compositions of this invention, HIV integrase, an enzyme required for viral integration, can be inactivated. It is important to clarify that since the reverse transcriptase of the viral particle is inactivated there will be no replication of the virus. The inactivated of HIV integrase would be an added safety feature. Without a functional integrase there is no possibility for the integration of HIV into the genetic material of the cell further ensuring the safety of the vaccine. The mechanism for integrase inactivation may be one of selective photolabeling using a (as azido group) bound to any of several compounds that are known to bind to HIV-integrase. Among these compounds are: anti-integrase oligonucleotides, L-chicoric acid, as well as a large number hydrazine derivative inhibitors.

Additionally, evaluating the efficacy of azido-diarylpyrimidine compositions in preventing or inhibiting retroviral infections may be performed using similar assays as described for evaluating the safety of immunogens. For example, the inability of virus particles to produce infection in susceptible cells or model animals in the presence or absence of azido-diarylpyrimidine may be evaluated.

Administration

The compositions disclosed herein may be administered by a variety of routes depending on the intended application. Pharmaceutical compositions for use in eliciting an immune response in a subject may be administered by, for example, intramuscular injection. Although other routes of injection, such as subcutaneous; as well as non-injection-based routes of administration, such as topical mucosal delivery, may be employed. It is important to consider different routes of administration, the intramuscular route will be the route of choice. The dose to be used for eliciting an immune response may be measured in viral particles and may have a range from the administration of 1 particle to $10^{20}$ particles. A preferred range of dosing is between $10^4$ particles and $10^8$ particles. Lower dose ranges may include doses of about 10, $10^2$, or $10^3$ particles. Preferred dose ranges may include doses of about $10^4$, $10^5$, $10^6$, $10^7$, or $10^8$ particles. Higher dose ranges may include doses of about $10^{10}$, $10^{12}$, $10^{14}$, $10^{16}$, $10^{18}$, or $10^{20}$ particles. The effective dosage may vary depending on the method of administration. For each dose to be tested, the schedule may consist of administration of a dose on days 0, 30, 60, and a booster dose at 180 days. Alternatively doses may be given weekly, every two weeks, or monthly for periods of one, two, three, four, five or six months. Doses may also be given every two months for a similar time. Periodic booster shots at intervals of 1-5 years may be desirable to maintain protective levels of immunity or generate sufficient immune response. Other administration schedules may be used and the invention contemplates any administration schedule that results in an effective response. In addition to monitoring for clinical safety, efficacy will be assessed by measuring the cellular and humoral immune response to the retrovirus.

Pharmaceutical compositions for use as microbicides will typically be administered topically, particularly to areas at risk for transmission of retrovirus particles. HIV, for example, may be transmitted via the mucous membranes of the vagina or rectum during sexual intercourse. Transmission via the eyes, breaks in the skin, and the mucosa of the oral cavity also posses a risk. Accordingly, a composition comprising azido-diarylpyrimidine may be applied, for example, to the vagina, rectum, and/or oral cavity prior to sexual intercourse in order to inactivate HIV present in the semen or mucosal secretions. In some embodiments, a composition comprising azido-diarylpyrimidine may be applied to the eyes, oral cavity, or breaks in the skin prior to or promptly after exposure to fluids (e.g., blood) or other materials that may contain retrovirus particles such as HIV particles. It is preferred that the time at which the composition is applied is in close proximity to the time of the exposure to the virus, and is preferably prior to exposure. Although infection may still be prevented if the composition is administered after exposure to the virus, preferably within a few minutes to a few hours after exposure, more preferably within about 15 minutes after exposure. These microbicidal compositions may comprise between about 0.1 to 50% by volume of the azido-diarylpyrimidine.

As mentioned above, azido-DAPY compounds can form an irreversible covalent bond in the hydrophobic pocket of reverse transcriptases when used in conjunction with UV light, thus resulting in the photoinactivation of reverse transcriptase. Accordingly, in certain embodiments the administration of the azido-DAPY composition further comprising irradiating the area to which the composition was applied. In certain embodiments, the azido-DAPY composition is irradiated within about 5 minutes of its application. Although, since azido-DAPY is capable for binding reverse transcriptase for some time without being irradiated, the irradiation can take place several hours or even several days after the azido-DAPY composition is applied to the treatment area.

HIV Vaccines

Historically, viral vaccines have been enormously successful in the prevention of infection by a particular virus. Therefore, when HIV was first isolated, there was a great amount of optimism that an HIV vaccine would be developed quickly. However, this optimism quickly faded because a number of unforeseen problems emerged. A discussion of the problems that an HIV vaccine must overcome is provided within Stott and Schild (1996) and is incorporated herein by reference.

First, HIV is a retrovirus, thus, during its growth cycle, proviral DNA is integrated in the host genome. In this form the virus is effectively protected from the immune response of the host and this feature of the virus suggests that effective vaccination must ideally prevent the initial virus-cell interaction following transmission. Few, if any, of the currently available successful viral vaccines against other infections achieve this level of protection. Secondly, HIV specifically targets and destroys T-helper lymphocytes, which form an essential component of the immune response. Thirdly, the virus is capable of extremely rapid antigenic variation which permits escape of the virus from immune responses. Fourthly, the majority of infections are acquired sexually via the genital or rectal mucosae, and infections of this route are generally considered difficult to prevent by vaccination. Finally, infection may be transmitted by virus-infected cells in which the proviral DNA is integrated and viral antigens are not expressed. Such a cell would not be recognized by immune responses to viral proteins and would therefore pass undetected. Few data are available to indicate how significant this mode of transmission is in the overall epidemiology of HIV-1. Nevertheless, it represents a potential route and one which some authorities believe cannot be blocked by vaccination (Sabin, 1992).

The immune response to HIV is composed of an initial cell mediated immune response followed by the subsequent development of neutralizing antibodies. Within weeks of infection, virus titers in the blood fall coincident with the induction of anti-HIV cellular and humoral immune responses. The fall in viremia correlates well with the appearance of anti-HIV major histocompatibility complex (MHC) class I-restricted $CD8^+$ cytotoxic T cells (Haynes et al., 1996). Evidence has shown a strong correlation of anti-HIV $CD4^+$ T cell responses and reduced viral loads (Rosenberg et al., 1997). Therefore, the presentation of HIV antigens in the context of MHC class II molecules to $CD4^+$ T cells may be the key aspect of the control of the HIV infection.

Rosenberg et al. (1997) suggest that in HIV-1 infection, HIV-specific CD4+ cells may be selectively eliminated. This may be due to the activation of these cells during high-level viremia, increasing their susceptibility to infection (Weissman et al., 1996; Stanley et al., 1996), or may be due to activation induced cell death during primary infection (Abbas, 1996). Nonetheless, increasing the virus-specific $CD4^+$ T cell response without infecting, or destroying, the responding cells may be an effective means of controlling viral loads. Therefore, some existing HIV vaccines may be ineffective because they do not provide presentation of HIV peptides in the context of MHC class II by antigen presenting cells.

Types of HIV vaccines include inactivated virus vaccines, live attenuated virus vaccines, virus subunit vaccines, synthetic particle vaccines, and naked DNA vaccines and are reviewed in Stott and Schild (1996), Schultz (1996), and Johnston (1997).

The first evidence that vaccination against immunodeficiency viruses was feasible came from early experiments using simple inactivated virus prevented the onset of disease when vaccinated animals were subsequently challenged (Desrosiers et al., 1989; Sutjipto et al., 1990). These results were confirmed and extended by Murphey-Corb et al. (1989) who showed that most animals immunized with formalin-inactivated virus were protected against infection with SIV. Similar results were subsequently obtained by several laboratories using virus-infected cells (Stott et al., 1990) or partially purified virus, inactivated by aldehydes (Putkonen et al., 1991, 1992; Johnson et al., 1992a; Le Grand et al., 1992), β-propiolactone (Stott et al., 1990) detergent (Osterhaus et al., 1992) or psoralin and UV light (Carlson et al., 1990). Several different isolates of SIV or infectious molecular clones derived from them were used to prepare the vaccine and challenge viruses. A wide variety of adjuvants were also employed. On every occasion vaccinated macaques were protected against infection by intravenous challenge of between 10-50 $MID_{50}$ (50% monkey infectious doses). Infections virus could not be recovered from the blood or tissues of the protected animals even when they were followed for prolonged periods of over 1 year. Even more impressive was the failure to detect proviral DNA in the lymphocytes of protected animals, indicating that there had been no integration of the challenge virus (Stott et al., 1990; Johnson et al., 1992a). It was thus clear that inactivated virus vaccines induced a powerful protective response in macaques. Unfortunately, the protection induced by inactivated SIV in macaques was not reproduced in chimpanzees vaccinated with inactivated HIV and challenged with HIV-1 (Warren and Doltshahi, 1993).

The genetic diversity of HIV has presented significant challenges to its treatment. The genetic diversity of HIV is due to the extremely high replication rate in infected individuals, the high rate of mutation caused by the error-prone reverse transcriptase, the substantial viral load, and selection within infected individuals (Doolittle, 1989; Ho et al., 1995; Piatek et al., 1993). Diversity is so great that the presence of closely related but not identical strains of HIV, known as quasispecies, commonly appear in a single, infected individual. The quasispecies may diverge increasingly over time and changes tend to be within the env gene, particularly the V3 region (Hwang et al., 1992). Although changes also may occur in the gag, pol, and accessory genes, these differences tend to be less substantial.

When significant changes accumulate and are seen in a large group of individuals, the strain is commonly considered a new family or new clade of HIV. Phylogenetic studies of HIV have shown that there are two major families of HIV, HIV-1 and HIV-2. Within the HIV-1 family there are two major antigenic groups, known as Group M (major) and Group O (outlier). Each of these two groups has in turn different subtypes or clades which, when analyzed, lead to the conclusion that both probably originated from two primordial viral ancestors. The group M is responsible for most of the HIV infections throughout the world and the group O is rarely found and confined to Cameroon, Gabon and France. There are at least nine subtypes or clades in the group M and of these, the subtype B is prevalent in the Western Hemisphere, while the subtypes A, C and D are in Africa. In Asia, the most frequently found subtypes are E, C and B, with the subtype E having a high prevalence in Southeast Asia. In India the prevalent subtype is C.

A vaccine comprising one clade may provide for the protection of infection by one or more other clades. An important concept when confronting what appears to be the very difficult challenge of antigenic variation is the understanding of the concept of critical antigenic conservation. By critical antigenic conservation it is meant that there is a critical number of epitopes which are found consistently in HIV. Although it is recognized that there are significant antigenic changes in the configuration of the envelope proteins, generally, the internal proteins have less sequence variation. It has been recently demonstrated that epitopes, of critical immunologic importance, are exposed or created as HIV begins to fuse with cell membranes. The fusion process results in a conformational change of envelope glycoproteins leading to the exposure of previously occult epitopes or the de novo formation of epitopes. The use of these fusion exposed epitopes has led to the preparation of antibodies which are capable of inhibiting the infectivity of multiple primary HIV isolates, including multiple genetic subtypes (Montefiori and Moore, 1999; LaCasse et al., 1999). The broad immunological protection elicited by the fusion exposed epitopes may explain the observation that people infected with HIV-1 virtually never have more than one subtype of virus.

These results indicate that once the immune system is exposed to HIV without integration of HIV in the genetic machinery of the host, the immune response will be effective and of a broad base. The non-infectious HIV particles disclosed herein mimic the antigenic structure and composition of natural infectious HIV particles. Thus, these non-infectious particles will penetrate susceptible cells, including cells of the immune system responsible for the generation of the immune response, in the identical fashion as infectious particles, that is by receptor/co-receptor binding and fusion. The receptor-mediated entry of the vaccine into cells results in exposure of the superior immunogenic epitopes and thereby facilitates the creation of a broad immunogenic response.

In addition to the recently described fusion exposed epitopes, the consistent regions of the env, gag, and pol together can lead to a critical mass of antigens responsible for the production of an effective immunological response to HIV and, which in fact, are present in nearly all types and subtypes of HIV. Thus, although it will be wise to use different wild types to create non-infectious particles and create a polyvalent vaccine, it is also possible that exposure of the immune system to a single type of inactivated HIV particle will be enough to generate a broad immune response.

The antigenic configuration of HIV is of the utmost importance since it is known that conformational epitopes can be located in variable regions of the HIV particle and can not be predicted from the analysis of the linear sequences of these regions. Therefore, it is of great importance that, in eliciting an effective protective immune response against HIV, the immune system is presented correct antigenic conformations. Non-infectious, virus-like particles have been produced via manipulations of the viral genome. For example, U.S. Pat. No. 6,080,408, incorporated herein by reference, discloses non-infectious virus-like particles wherein RT has been made inactive by virtue of deletions and sequence changes in the viral genome. Rovinski also discloses other methods of making non-infectious, virus-like particles, (or pseudovirions), that involve alterations to other genes of the HIV genome, expression of a subset of HIV virion components, and heat-inactivation of sera from HIV infected individuals. U.S. Pat. No. 6,017,543 discloses methods using formalin, psoralen, beta-propriolactone, alone and in combination, as well as exposure to gamma radiation.

Substantial evidence indicates that dendritic cells ("DC") present in epithelial tissues (e.g., Langerhans cells) are the initial cells infected with HIV after mucosal exposure to the virus (Cameron et al., 1996; Knight, 1996). The bone marrow-derived DC are a class of antigen-presenting cells ("APC") that survey epithelial tissues for antigens and are efficient stimulators of both B and T lymphocytes. Unlike B cells, T cells cannot directly recognize antigens and require that antigens be processed and presented by APCs (Banchereau and Steinman, 1998). Intracellular processing of antigens to peptide fragments results in binding to MHC class 1 molecules and a CD8+ cytotoxic T cell response. In contrast, antigens that enter DC by the endocytic pathway generally bind to MHC class II molecules the elicitation of a CD4+ helper T cell response (Banchereau and Steinman, 1998).

Inactivated HIV viral particles will be processed and presented by DC as long as the inactivated HIV particles are preserved in its antigenic composition and can access the cytoplasm of the dendritic cells. Both of these conditions are met by the present invention. That is, the inactivated particles have a preserved envelope structure and thus will access the cytoplasm of the dendritic cell by a process of micropinocytosis or mannose-receptor mediated uptake. DC that have been exposed to the inactivated HIV particles will migrate to the lymph nodes where they will interact with T-cells presenting MHC-antigens complexes to both memory and naive T-cells (see Banchereau and Steinman, 1998; Bender et al., 1995). This process will lead to the development of an effective anti-HIV MHC-I restricted CD8+ T-cell response. Cytotoxic CD8+ T cells are recognized as having an important role in controlling HIV invention (Musey et al., 1997; Oldstone, 1997).

Dendritic cells also have CD4/HIV co-receptors and thus can be infected by HIV. This infectious process is independent of the capture and processing of HIV for antigenic presentation and initiation of the MHC class I restricted immunological response (Blauvelt et al., 1997). But since the inactivated particles are non-infections, the process of penetration through a receptor mechanism will allow the production of a MHC-II restricted response. Thus DC cells will activate and expand CD4+ T helper cells, which in turn will induce B cell growth and antibody production. This MHC class II response will thereby complement the MHC class I restricted immune response by establishing an effective cytotoxic and humoral response as well as an effective immunological memory.

The immunogenic compositions disclosed herein may be comprised of inactivated viruses from one or more clades of HIV. In certain embodiments, the inactivated viruses may be comprised of inactivated viruses of the clade or clades with which an individual is most likely to come in contact based on his or her geographical area.

Furthermore, because inactivated viruses may be produced cheaply and rapidly by the methods disclosed herein, an individual may be vaccinated with inactivated virus or even inactivated HIV infected cells from the individual most likely to pass or have passed the virus to the individual. For example, an HIV-negative person may be vaccinated with inactivated HIV or inactivated HIV-infected cells from an HIV-positive individual with which the HIV-negative individual plans to or has already come in sexual contact. An example of such a HIV-negative individual could be someone married to someone who is HIV-positive. Additionally, these "personal" vaccines may have the benefit of also having cellular (nonviral) surface proteins from the individual passing the virus. The immune response to cellular surface proteins incorporated into the virus particles, which include MHC antigens, have been shown to confer protection from future challenges from viruses grown in the same cell line (Stott et al., 1991).

Animal Models

A number of different animal model systems for HIV infection have been employed (Kindt et al., 1992). Non-human primates such as chimpanzees and pig-tailed macaques can be infected by HIV-1. Although CD4+ cells are not depleted in these systems, the animals are detectably infected by the virus and are useful in determining the efficacy of HIV vaccines. Small animal models include chimeric models that involve the transplantation of human tissue into immunodeficient mice. One such system is the hu-PBL-SCID mouse developed by Mosier et al. (1988). Another is the SCID-hu mouse developed by McCune et al. (1988). Of the two mouse models, the SCID-hu mouse is typically preferred because HIV infection in these animals is more similar to that in humans. SCID-hu mice implanted with human intestine have been shown to be an in vivo model of mucosal transmission of HIV (Gibbons et al., 1997). The ability of the inactivated HIV particles to elicit neutralizing antibodies can be measured in mice as previously described (LaCasse et al., 1999). The ability of sera to neutralize a range of HIV isolates can be tested using U87-CD4 cells expressing either CCR5 or CXCR4 coreceptors or by using an peripheral blood lymphocyte culture assay (LaCasse et al, 1999, LaCasse et al., 1998; Follis et al., 1998). Methods of constructing mammals with human immune systems are described in U.S. Pat. Nos. 5,652, 373, 5,698,767, and 5,709,843.

Retroviral infections may also be studied using animals infected by other retroviral pathogens. Examples of such pathogens include feline leukemia virus, feline immunodeficiency virus, avian leukosis virus, bovine leukemia virus, and rous sarcoma virus.

The animals will be inoculated with the immunogens of the present invention and later challenged with a dose of infectious virus. Efficacy of the immunogens in producing a protective response will be determined by methods known by those of skill in the art. Generally, a variety of parameters associated with retrovirus infection may be tested and a comparison may be made between vaccinated and non-vaccinated animals. In the context of HIV, such parameters include viremia, detection of integrated HIV in blood cells, loss of CD4+ cells, production of HIV particles by PBMC, etc. The immunogens will be considered effective if there is a significant reduction of signs of infection in the vaccinated versus the non-vaccinated groups.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Early and Irreversible Inactivation of HIV-1 By Azido-DAPY and UV Light Exposure Time-exposure studies demonstrated an early and irreversible inactivation of HIV-1 by azido-DAPY+UV light exposure treatment that was not observed in the control groups where DAPY without the azido group was used.

Figure 2:
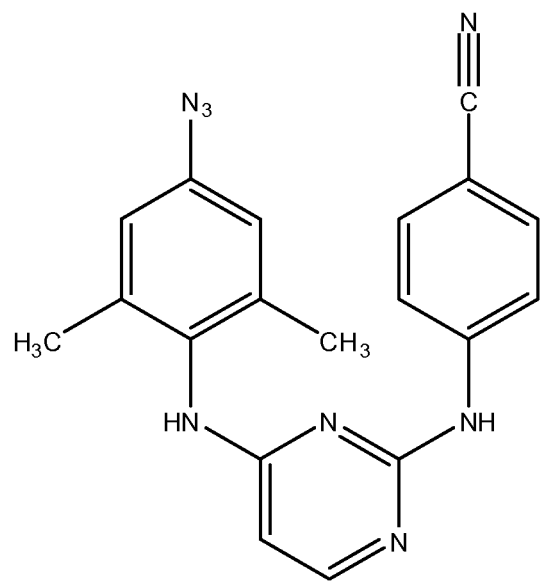
FIG. 2. Chemical structure of an azido-DAPY compound.

MT-2 cells were contacted with HIV-1 TCID$_{50}$, and 0, 2, 10, 20, or 50 nM of either DAPY (TMC120-R147681) or azido-DAPY were placed on 50μ/well plates. The plates were placed on ice for 20 minutes and then irradiated at 7.5 cm from a UV light source (UVP lamp model UVGL-25) that provides UV light at a wavelength of 365 nm and an intensity of 1.14 W/cm$^2$ for a period of 20 minutes. Studies of HIV-1 infected MT-2 cells contacted with DAPY but not UV irradiated, and HIV-1 infected MT-2 cells that were irradiated but not contacted with DAPY or azido-DAPY were also performed. The structure of the azido-DAPY used in these studies in provided in FIG. 2. The results are shown in FIG. 3.

The inactivation of HIV was evaluated by a reverse transcriptase activity assay as described by Xu et al. (2009). The measurements are provided in counts per minute (cpm). As shown in FIG. 3, treatment with 10 nM azido-DAPY and UV light inactivated the HIV for at least 30 days after treatment. In contrast, 10 nM DAPY (non-azido DAPY), either with or without UV light treatment, lost its capacity to inactivate the HIV-1 reverse transcriptase within 16 days of treatment.

At concentrations higher than 10 nM, observable differences between DAPY and the azido-DAPY diminish due to the excess of both compounds relative to the amount of virus to be inactivated. As noted above, however, at 10 nM of DAPY and azido-DAPY the difference in inactivation is striking, with azido-DAPY inactivating the HIV-1 reverse transcriptase in a permanent manner while DAPY, DAPY+UV, and UV alone all show the inability to produce a permanent inactivation of reverse transcriptase.

All of the compositions and methods disclosed and claimed herein can be made and executed without undue experimentation in light of the present disclosure. While the compositions and methods may be described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,041,078
U.S. Pat. No. 5,516,629
U.S. Pat. No. 5,593,823
U.S. Pat. No. 5,652,373
U.S. Pat. No. 5,698,767
U.S. Pat. No. 5,709,843
U.S. Pat. No. 6,017,543
U.S. Pat. No. 6,080,408
U.S. Pat. No. 6,383,806
U.S. Pat. No. 6,503,753
U.S. Pat. No. 6,649,410
U.S. Pat. No. 6,653,130
Abbas, *Cell*, 84:655, 1996.
American Foundation for AIDS Research's HIV Experimental Vaccine Directory, 1:2, 1998.
Bader et al., *Proc. Natl. Acad. Sci. U.S.A.*, 88:6740-6744, 1991.
Balzarini et al., *Antimicrob. Agents Chemother.*, 40:1454-1466, 1996.
Balzarini et al., *Proc. Natl. Acad. Sci. U.S.A.*, 92:5470-5474, 1995.
Banchereau and Steinman, *Nature*, 392:245-252, 1998.
Bender et al., *J. Exp. Med.*, 1663-1671, 1995.
Blauvelt et al., *J. Clin. Invest.*, 100(8):2043-2053, 1997.
Cameron et al., *J. Leukocyte Biol.*, 59:158-171, 1996.
Carlson et al., *AIDS Res. Hum. Retrovir.*, 6:1239-46, 1990.
Carroll et al., *J. Biol. Chem.*, 268:276-281, 1993.
Cruz and Uckun, *J. Antimicrobial Chemotherapy*, 57:411-423. 2006.
Das et al., *J. Med. Chem.*, 47:2550-2560, 2004.
Desrosiers et al., *Proc. Natl. Acad. Sci. USA*, 86:6353-7, 1989.
Doolittle, *Nature*, 339:338, 1989.
Follis et al., *J. Virol.*, 72:7603-7608, 1998.

Furman et al., *Proc. Natl. Acad. Sci. U.S.A.*, 83:8333-8337, 1986.
Gibbons et al., *AIDS Res Hum Retroviruses*, 13(17):1453-1460, 1997.
Goldman et al., *Proc. Natl. Acad. Sci. U.S.A.*, 88:6863-6867, 1991.
Grob et al., *AIDS Res. Hum. Retroviruses*, 8:145-152, 1992.
Haynes et al., *Science* 271:324-328, 1996.
Ho et al., *Nature*, 373:123, 1995.
Hwang et al., *Science*, 257:535, 1992.
Johnson et al., *Proc. Natl. Acad. Sci. USA*, 89:2175-9, 1992a.
Johnston, *Hospital Practice*, 32(5):125-8, 131-40, 1997.
Kindt et al., In: *Advances in Immunology*, Acedemic Press, Inc., NY, 52:425-474, 1992
Knight, *AIDS (Lond.)*, 10:807-817, 1996.
LaCasse et al., *J. Virol.* 72:2491-2495, 1998.
LaCasse et al., *Science*, 283:357-362, 1999.
Le Grand et al., 1992
Ludovici et al., *Bioorganic Medicinal Chem. Lett.*, 11:2235-2239. 2001.
McCune et al., *Science*, 241:1632-1639, 1988.
Merluzzi et al., *Sci.*, 20:1411-1413, 1990.
Montefiori and Moore, *Science*, 283:336-337, 1999.
Mosier et al., *Nature*, 335:256-259, 1988.
Murphey-Corb et al., *Science*, 246:1293-7, 1989.
Musey et al., *N. Eng. J. Med.*, 337(18):1267-1274, 1997.
Oldstone, *N. Eng. J. Med.*, 337:1306-1308, 1997.
Osterhaus et al., *AIDS Res. Hum. Retrovir.*, 8:1507-10, 1992.
PCT Application No. 91/09603
Piatek et al., *Science*, 259:1749, 1993.
Putkonen et al., *AIDS Res. Hum. Retrovir.*, 7:271-7, 1991.
Putkonen et al., *J. Med. Primatol.*, 21:108-12, 1992.
Rosenberg et al., *Science* 278:1447-1450, 1997.
Sabin, *Proc. Natl. Acad. Sci. USA*, 89:8852-5, 1992.
Schultz, *Advances Experi. Med. Biology*, 397:79-90, 1996.
Stanley et al., *N. Engl. J. Med.*, 334:1222, 1996.
Stott and Schild, *J. Antimicrobial Chemo.*, 37(B):185-198, 1996.
Stott et al., *Lancet*, 336:1538-41, 1990.
Stott et al., *Nature*, 353:393, 1991.
Sutjipto et al., *J. Virol.*, 64:2290-7, 1990.
Warren and Doltshahi, *J. Med. Primatol.*, 22:203-35, 1993.
Weissman et al., *J. Exp. Med.*, 183:687, 1996.
Xu et al., *Antimicrob. Agents Chemother.*, 53(11):4667-72, 2009.
Yang et al., *J. AIDS and Human Retrovirology*, 17:27-34, 1998.
Zhang et al., *AIDS Res. Hum. Retroviruses* 9:1287-1296, 1993.
Zhang et al., *J. Virol.*, 70:2809-2824, 1996.

The invention claimed is:

1. A method of making an HIV particle comprising an inactive reverse transcriptase comprising:
   contacting an HIV particle comprising a reverse transcriptase with an azido-diarylpyrimidine of formula (I):

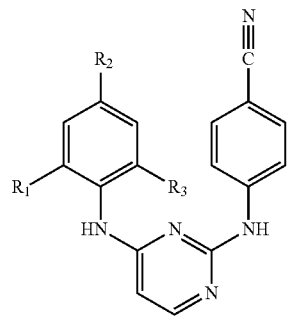

wherein $R_1$, $R_2$, and $R_3$ are independently $N_3$ or lower alkyl, with the proviso that at least one of $R_1$, $R_2$, and $R_3$ is $N_3$; and
   irradiating the HIV particle comprising the reverse transcriptase and the azido-diarylpyrimidine with ultraviolet light to inactivate the reverse transcriptase.

2. A composition comprising an HIV particle and an azido-diarylpyrimidine of formula (I):

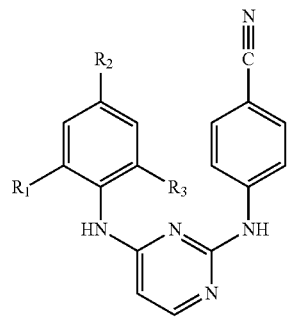

wherein $R_1$, $R_2$, and $R_3$ are independently $N_3$ or lower alkyl, with the proviso that at least one of $R_1$, $R_2$, and $R_3$ is $N_3$.

3. A method of inactivating an HIV particle comprising:
   contacting an HIV particle with an azido-diarylpyrimidine of formula (I):

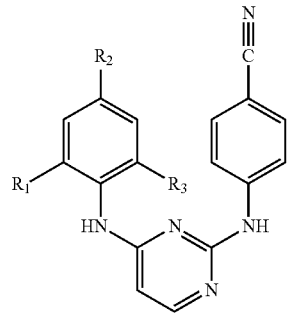

wherein $R_1$, $R_2$, and $R_3$ are independently $N_3$ or lower alkyl, with the proviso that at least one of $R_1$, $R_2$, and $R_3$ is $N_3$; and
   irradiating the HIV particle and the azido-diarylpyrimidine with ultraviolet light to inactivate the HIV particle.

4. A method of eliciting an immune response comprising administering an HIV particle comprising a reverse transcriptase covalently bound to an azido-diarylpyrimidine to a subject, wherein an immune response is elicited in the subject, wherein the azido-diarylpyrimidine has the formula of formula (I):

(I)

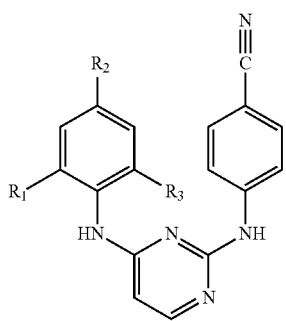
wherein $R_1$, $R_2$, and $R_3$ are independently $N_3$ or lower alkyl, with the proviso that at least one of $R_1$, $R_2$, and $R_3$ is $N_3$.

5. The method of claim 4, wherein the subject is human.

6. The method of claim 1, wherein $R_2$ and $R_3$ are $CH_3$ and $R_1$ is $N_3$.

7. The method of claim 1, wherein $R_1$ and $R_3$ are $CH_3$ and $R_2$ is $N_3$.

8. The method of claim 1, wherein $R_1$ and $R_2$ are $CH_3$ and $R_3$ is $N_3$.

9. The composition of claim 2, wherein $R_2$ and $R_3$ are $CH_3$ and $R_1$ is $N_3$.

10. The composition of claim 2, wherein $R_1$ and $R_3$ are $CH_3$ and $R_2$ is $N_3$.

11. The composition of claim 2, wherein $R_1$ and $R_2$ are $CH_3$ and $R_3$ is $N_3$.

12. The method of claim 3, wherein $R_2$ and $R_3$ are $CH_3$ and $R_1$ is $N_3$.

13. The method of claim 3, wherein $R_1$ and $R_3$ are $CH_3$ and $R_2$ is $N_3$.

14. The method of claim 3, wherein $R_1$ and $R_2$ are $CH_3$ and $R_3$ is $N_3$.

15. The method of claim 4, wherein $R_2$ and $R_3$ are $CH_3$ and $R_1$ is $N_3$.

16. The method of claim 4, wherein $R_1$ and $R_3$ are $CH_3$ and $R_2$ is $N_3$.

17. The method of claim 4, wherein $R_1$ and $R_2$ are $CH_3$ and $R_3$ is $N_3$.

* * * * *